United States Patent
Lee et al.

(10) Patent No.: US 10,714,694 B2
(45) Date of Patent: Jul. 14, 2020

(54) DELAYED FLUORESCENCE MATERIAL AND ORGANIC LIGHT EMITTING DEVICE HAVING THE DELAYED FLUORESCENCE MATERIAL

(71) Applicant: RESEARCH & BUSINESS FOUNDATION SUNGKYUNKWAN UNIVERSITY, Suwon-si, Gyeonggi-do (KR)

(72) Inventors: Junyeob Lee, Yongin-si (KR); Yirang Im, Daejeon (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 15/789,209

(22) Filed: Oct. 20, 2017

(65) Prior Publication Data

US 2018/0114924 A1 Apr. 26, 2018

(30) Foreign Application Priority Data

Oct. 21, 2016 (KR) .................. 10-2016-0137574

(51) Int. Cl.

| H01L 51/54 | (2006.01) |
| C09K 11/06 | (2006.01) |
| H01L 51/00 | (2006.01) |
| C07D 487/06 | (2006.01) |
| H01L 51/50 | (2006.01) |

(52) U.S. Cl.
CPC ........ *H01L 51/0072* (2013.01); *C07D 487/06* (2013.01); *C09K 11/06* (2013.01); *H01L 51/0067* (2013.01); *C09K 2211/1018* (2013.01); *H01L 51/5012* (2013.01); *H01L 2251/5376* (2013.01)

(58) Field of Classification Search
CPC . C09K 11/06; C09K 2211/00; C09K 2211/10; C09K 2211/1018; C09K 2211/1022; C09K 2211/1029; C07D 209/82; C07D 487/00; C07D 487/02; C07D 487/06; H01L 51/0032; H01L 51/005; H01L 51/0062; H01L 51/0067; H01L 51/0069; H01L 51/0071; H01L 51/0072; H01L 51/50; H01L 51/5012; H01L 51/5016; H01L 2251/00; H01L 2251/50; H01L 2251/53; H01L 2251/5376
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

U.S. PATENT DOCUMENTS

2012/0241732 A1* 9/2012 Endo ................. C09B 57/00 257/40

FOREIGN PATENT DOCUMENTS

| KR | 20150002219 A | * | 1/2015 |
| KR | 20150114791 A | * | 10/2015 |
| KR | 20150114791 A | | 10/2015 |
| KR | 20160045569 A | | 4/2016 |

OTHER PUBLICATIONS

Machine translation of KR2015-0114791. (Year: 2015).*
Machine translation of KR2015-0002219. (Year: 2015).*
Chen et al., "Understanding the Control of Singlet-Triplet Splitting for Organic Exciton Manipulating: A combined theoretical and experimental approach", Scientific Reports, Jul. 10, 2015, 5:10923.

* cited by examiner

*Primary Examiner* — Andrew K Bohaty
(74) *Attorney, Agent, or Firm* — NSIP Law

(57) ABSTRACT

A delayed fluorescence material is disclosed. The delayed fluorescence material has a molecular structure that includes an electron donor unit that donates electrons; and an electron acceptor unit that is coupled to the electron donor unit and accepts electrons, wherein the electron acceptor unit includes an indolocarbazole group having at least one acceptor functional-group bound to the indolocarbazole group. Thus, the delayed fluorescence material exhibits high structural and thermal stability as well as high quantum efficiency.

10 Claims, 3 Drawing Sheets

DELAYED FLUORESCENCE MATERIAL AND ORGANIC LIGHT EMITTING DEVICE HAVING THE DELAYED FLUORESCENCE MATERIAL

CROSS-REFERENCE TO RELATED APPLICATIONS

This application claims the benefit under 35 USC § 119(a) of Korean Patent Application No. 10-2016-0137574 filed on Oct. 21, 2016 in the Korean Intellectual Property Office, the entire disclosure of which is incorporated herein by reference for all purposes.

BACKGROUND

Field of the Present Disclosure

The present disclosure relates to a delayed fluorescence material emitting over a long period of time, and an organic electroluminescent device comprising the same.

Discussion of Related Art

In order to commercialize an organic light emitting device, it is necessary to improve the efficiency of a light emitting material. For this purpose, studies on phosphorescent and delayed fluorescent materials have been actively carried out. However, although the phosphorescent material achieves the high luminous efficiency, a cost of a metal complex required to realize phosphorescence is high and the lifetime thereof is short.

In connection with the delayed fluorescent material, a recent publication in Nature (2012, 492, 234) and JACS (2012, 134, 14706) introduces the concept of Thermally Activated Delayed Fluorescence (TADF) by which a high efficiency green fluorescent material with high external quantum efficiency is achieved. The TADF concept represents the phenomenon that reverse transfer of energy from an excited triplet state to an excited singlet state is caused by thermal activation, leading to fluorescence emission. Since the light emission is generated via the triplet state in the TADF and, thus, the light emission has a long lifetime, this is generally referred to as delayed fluorescence. The combination of electron donor units and electron acceptor units to reduce the energy gap between the singlet and the triplet excited states may lead to the delayed fluorescence material with high efficiency. The delayed fluorescent material may use both fluorescence and phosphorescence. Therefore, the delayed fluorescent material may remove the problem in terms of the external quantum efficiency as the conventional fluorescent material has. The delayed fluorescent material may not contain the metal complex, thereby remove the problem of the expensive cost of phosphorescence materials.

However, in developing the delayed fluorescent material, it is difficult to design delayed fluorescent materials having various molecular structures due to limitation of the kinds of electron acceptor units. Therefore, the development of a new electron acceptor unit is required.

SUMMARY

This Summary is provided to introduce a selection of concepts in a simplified form that are further described below in the Detailed Description. This Summary is not intended to identify all key features or essential features of the claimed subject matter, nor is it intended to be used alone as an aid in determining the scope of the claimed subject matter.

The present disclosure is to provide a delayed fluorescence material with a molecular structure containing, as an electron acceptor unit, an indolocarbazole group having at least one acceptor functional group bound thereto such that the delayed fluorescence material is structurally and thermally stable and has highly luminous efficiency.

The present disclosure is further to provide an organic light emitting device comprising the delayed fluorescence material.

In a first aspect of the present disclosure, there is provided a delayed fluorescence material having a molecular structure, wherein the molecular structure includes an electron donor unit and an electron acceptor unit coupled to the electron donor unit, wherein the electron acceptor unit includes an indolocarbazole group having at least one acceptor functional-group bound to the indolocarbazole group.

In a first embodiment of the first aspect, the molecular structure has one of following structural formulas 1-1 to 1-6:

[Structural formula 1-1]

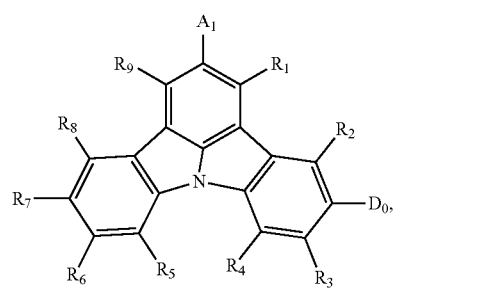

[Structural formula 1-2]

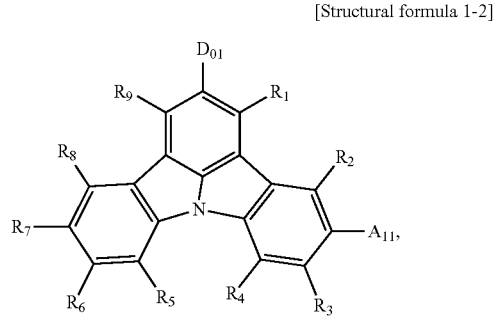

1p;2p

[Structural formula 1-3]

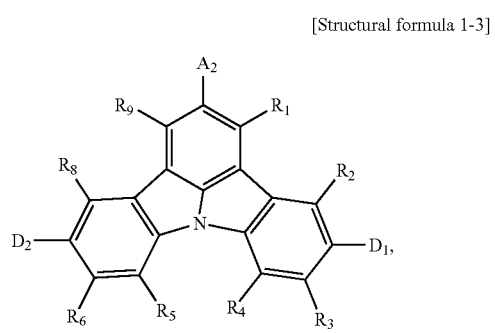

[Structural formula 1-4]

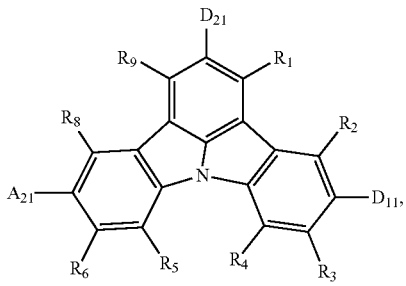

[Structural formula 1-5]

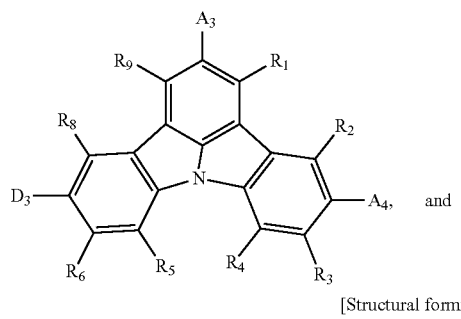

[Structural formula 1-6]

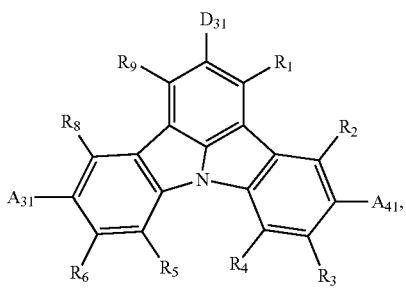

wherein each of $D_0$, $D_{01}$, $D_1$, $D_2$, $D_{11}$, $D_{21}$, $D_3$ and $D_{31}$ individually represents the electron donor unit, wherein each of $A_1$, $A_{11}$, $A_2$, $A_{21}$, $A_3$, $A_4$, $A_{31}$ and $A_{41}$ individually represents the acceptor functional-group, wherein each of $R_1$ to $R_9$ individually represents one selected from a group consisting of hydrogen, deuterium, an alkyl group having 1 to 60 carbon atoms, an alkylthio group having 1 to 10 carbon atoms, an alkyl-substituted amino group having 1 to 10 carbon atoms, an aralkyl group having 7 to 20 carbon atoms, a diarylamino group having 12 to 24 carbon atoms, an alkoxycarbonyl group having 2 to 10 carbon atoms, an alkylsulfonyl group having 1 to 10 carbon atoms, a haloalkyl group having 1 to 10 carbon atoms, an amino group, an alkylamide group having 2 to 10 carbon atoms, a trialkylsilyl group having 3 to 20 carbon atoms, a trialkylsilylalkyl group having 4 to 20 carbon atoms, an alkenyl group having 2 to 60 carbon atoms, a trialkylsilyl-alkenyl group having 5 to 20 carbon atoms, an alkynyl group having 2 to 60 carbon atoms, a trialkylsilylalkynyl group having 5 to 20 carbon atoms, a cyano group, a nitro group, an aryl group having 6 to 60 carbon atoms, a heteroaryl group having 3 to 60 carbon atoms, an alkoxy group having 1 to 60 carbon atoms, an aryloxy group having 6 to 60 carbon atoms, an arylalkyl group having 7 to 60 carbon atoms, a heteroarylalkyl group having 3 to 60 carbon atoms, a cycloalkyl group having 3 to 60 carbon atoms, a heterocycloalkyl group having 1 to 60 carbon atoms, an alkylsilyl group having 3 to 60 carbon atoms, an arylsilyl group having 3 to 60 carbon atoms, a heteroarylsilyl group having 1 to 60 carbon atoms, and a substituted or unsubstituted aromatic 6-membered heterocycle having 3 to 30 carbon atoms, wherein at least two of $R_1$ to $R_9$ are the same or different, or adjacent two of $R_1$ to $R_9$ are coupled to form a ring.

In a second embodiment of the first aspect, each of $D_0$, $D_{01}$, $D_1$, $D_2$, $D_{11}$, $D_{21}$, $D_3$ and Dai individually includes a functional-group compound derived from one selected from a group consisting of compounds having following structural formulas 2-1 to 2-52 respectively:

[Structural formula 2-1]

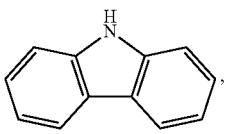

[Structural formula 2-2]

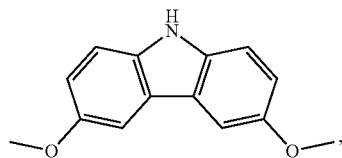

[Structural formula 2-3]

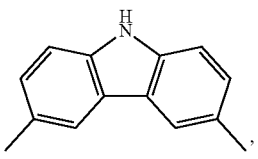

[Structural formula 2-4]

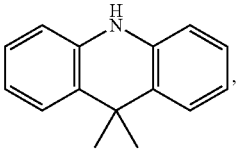

[Structural formula 2-5]

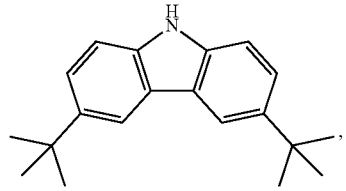

[Structural formula 2-6]

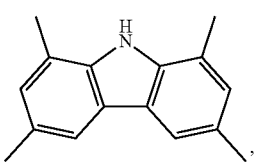

[Structural formula 2-7]

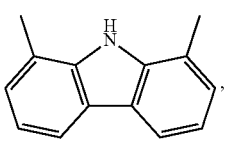

[Structural formula 2-8]

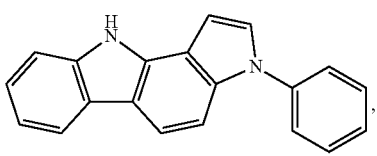

[Structural formula 2-9]
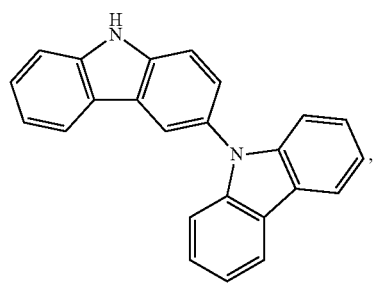
[Structural formula 2-10]
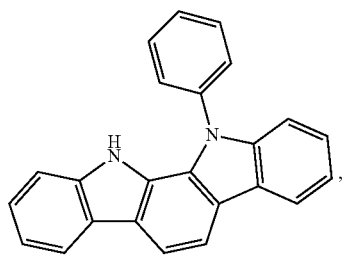
[Structural formula 2-11]
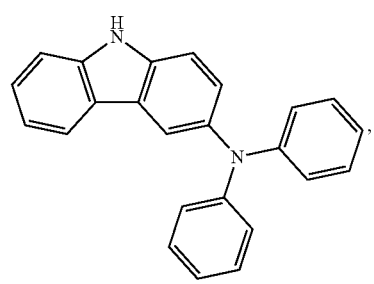
[Structural formula 2-12]
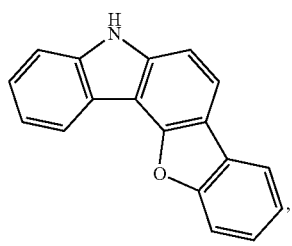
[Structural formula 2-13]
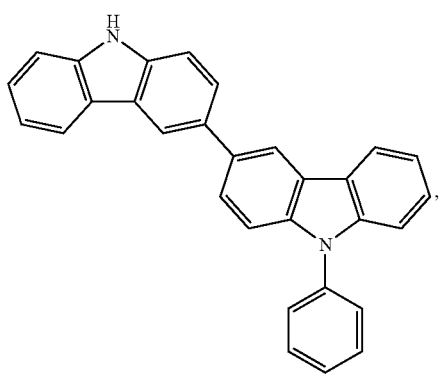
[Structural formula 2-14]
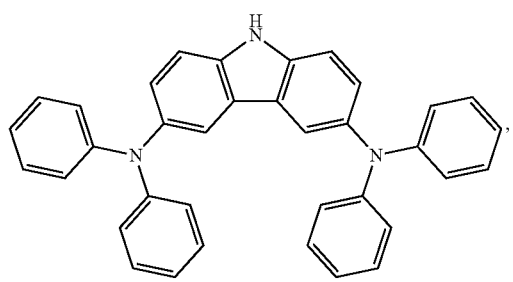
[Structural formula 2-15]
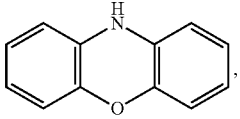
[Structural formula 2-16]
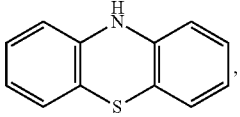
[Structural formula 2-17]
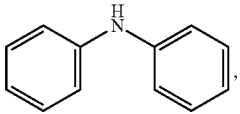
[Structural formula 2-18]
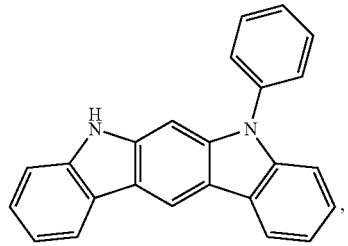
[Structural formula 2-19]
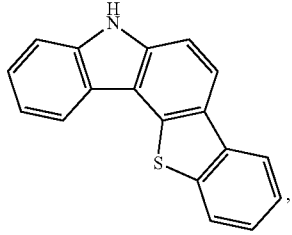
[Structural formula 2-20]
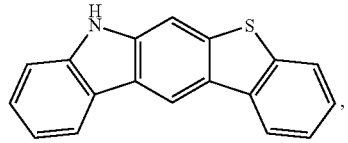
[Structural formula 2-21]
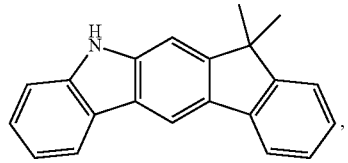

[Structural formula 2-22]
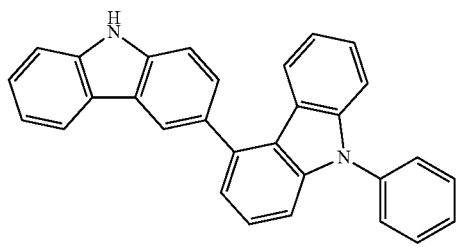
[Structural formula 2-23]
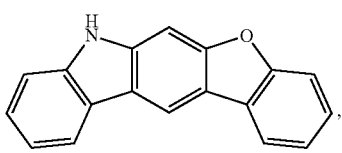
[Structural formula 2-24]
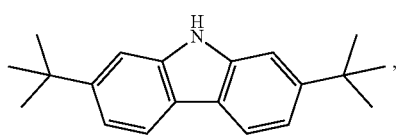
[Structural formula 2-25]
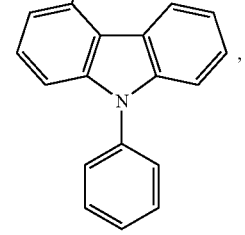
[Structural formula 2-26]
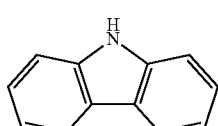
[Structural formula 2-27]
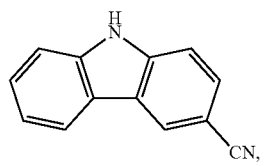
[Structural formula 2-28]
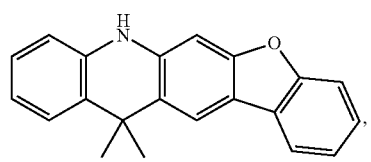
[Structural formula 2-29]
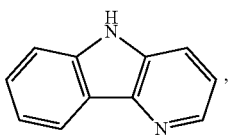
[Structural formula 2-30]
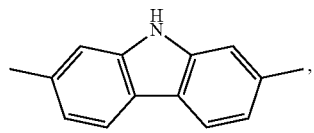
[Structural formula 2-31]
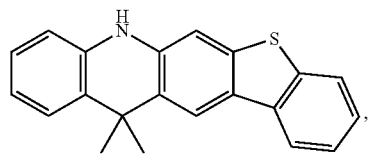
[Structural formula 2-32]
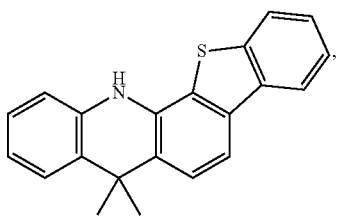
[Structural formula 2-33]
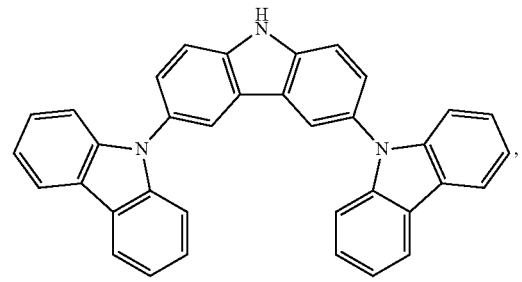
[Structural formula 2-34]
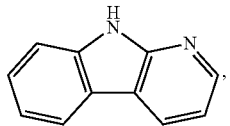
[Structural formula 2-35]
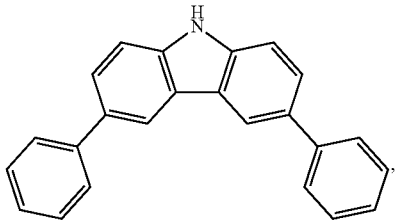
[Structural formula 2-36]
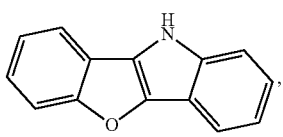

[Structural formula 2-37]
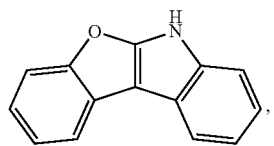
[Structural formula 2-38]
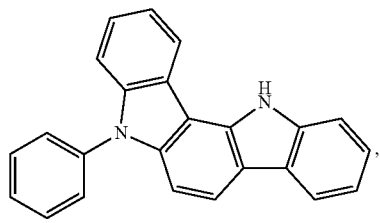
[Structural formula 2-39]
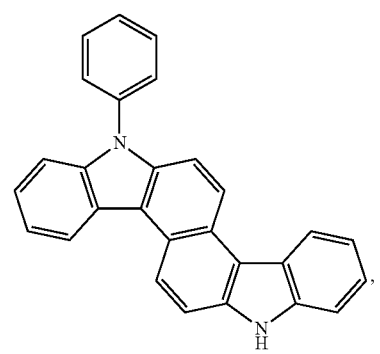
[Structural formula 2-40]
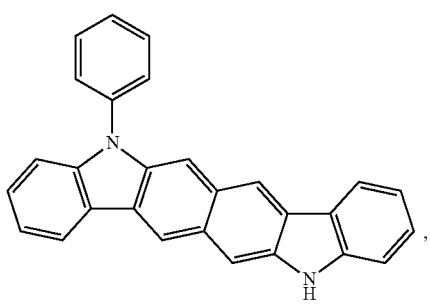
[Structural formula 2-41]
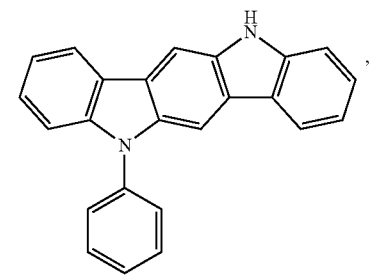
[Structural formula 2-42]
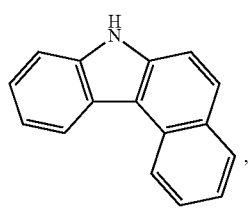
[Structural formula 2-43]
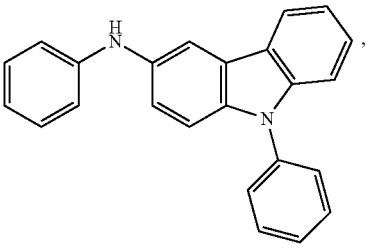
[Structural formula 2-44]
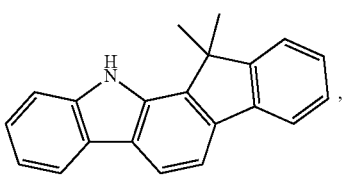
[Structural formula 2-45]
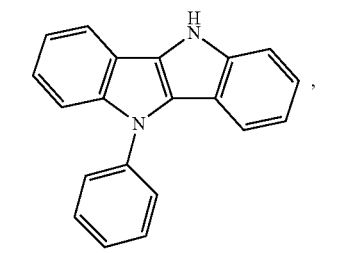
[Structural formula 2-46]
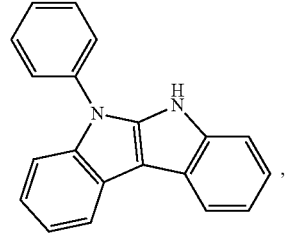
[Structural formula 2-47]
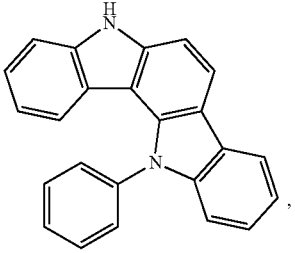
[Structural formula 2-48]
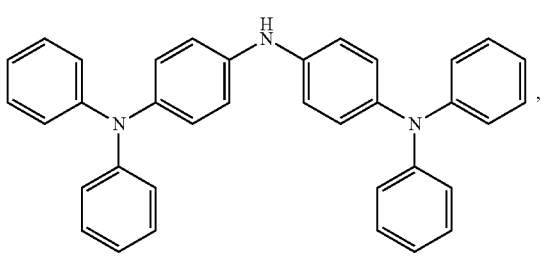
[Structural formula 2-49]
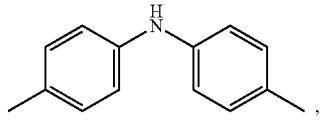

-continued

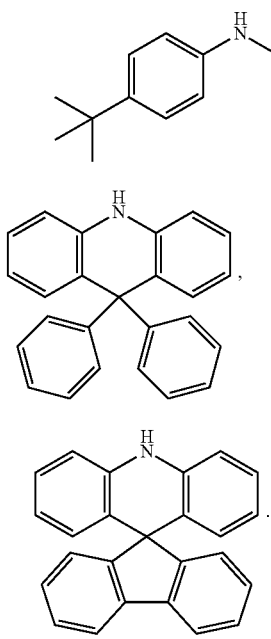

[Structural formula 2-50]

[Structural formula 2-51], and

[Structural formula 2-52].

tional-group compound derived from one selected from a group consisting of compounds having following structural formulas 3-1 to 3-4 respectively:

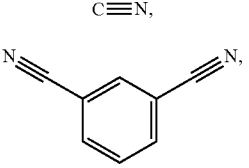

[Structural formula 3-1]

[Structural formula 3-2]

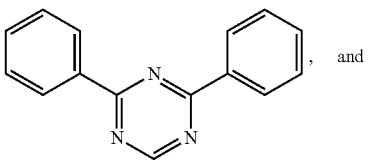

[Structural formula 3-3], and

[Structural formula 3-4]

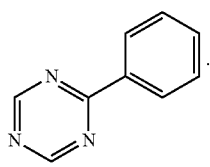

In a third embodiment of the first aspect, each of $A_1$, $A_{11}$, $A_2$, $A_{21}$, $A_3$, $A_4$, $A_{31}$ and $A_{41}$ individually includes a functional-group compound derived from one selected from a group consisting of compounds having following structural formulas 3-1 to 3-4 respectively:

In a fourth embodiment of the first aspect, the molecular structure has one of following structural formulas 4 to 15:

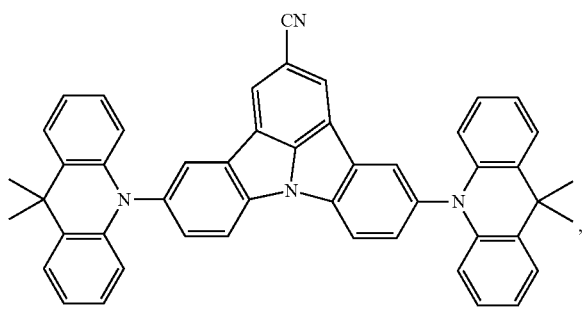

[Structural formula 4]

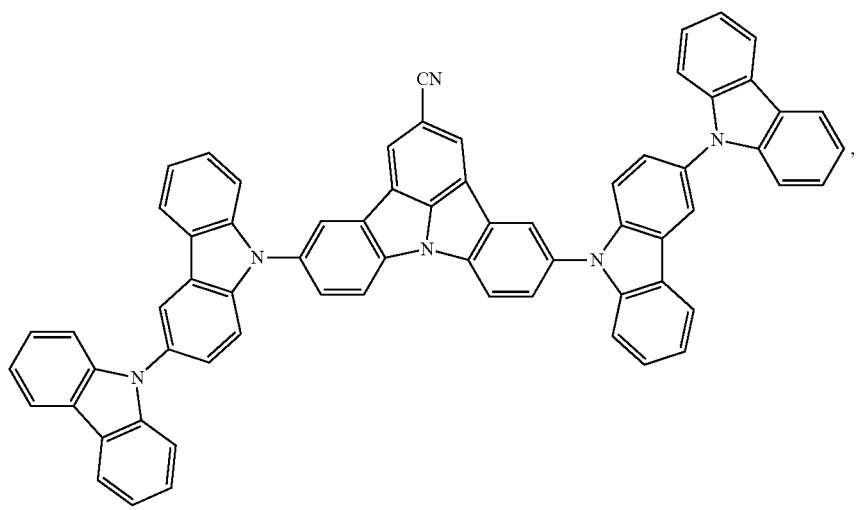

[Structural formula 5]

-continued
[Structural formula 6]
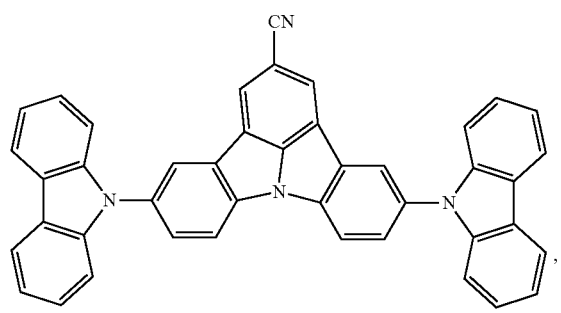,
[Structural formula 7]
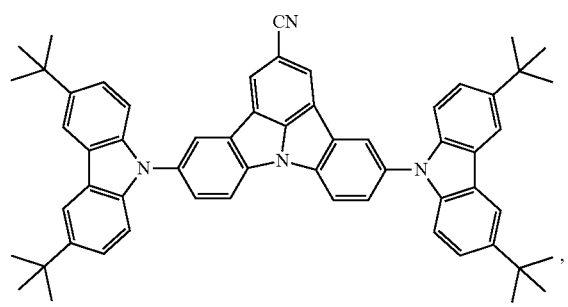,
[Structural formula 8]
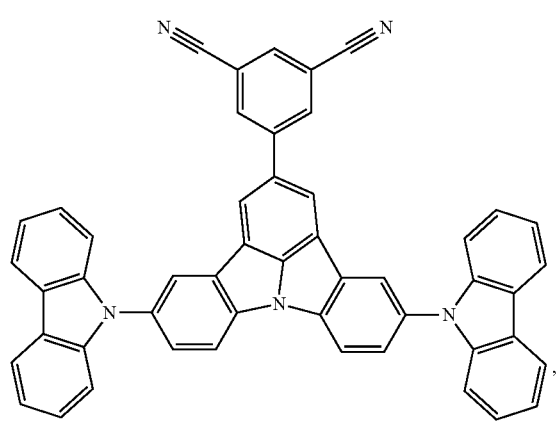,
[Structural formula 9]
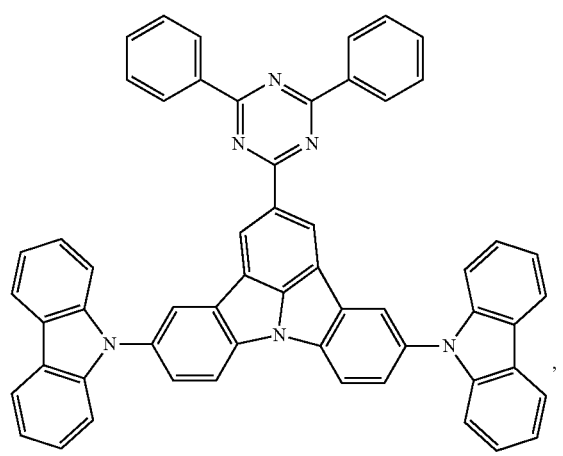,
[Structural formula 10]
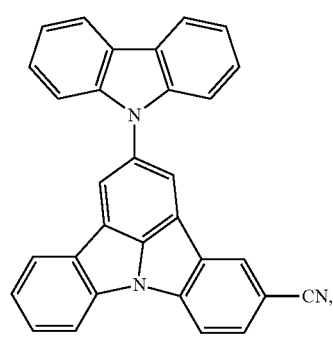,
[Structural formula 11]
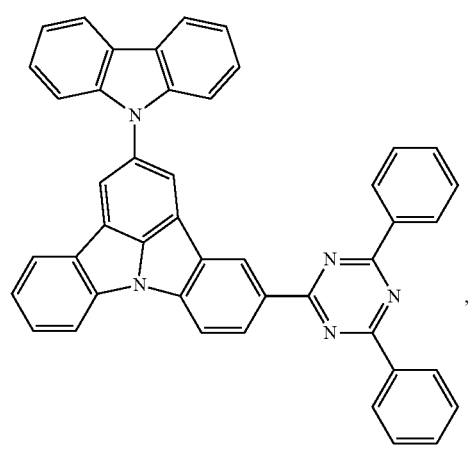, -continued

[Structural formula 12]

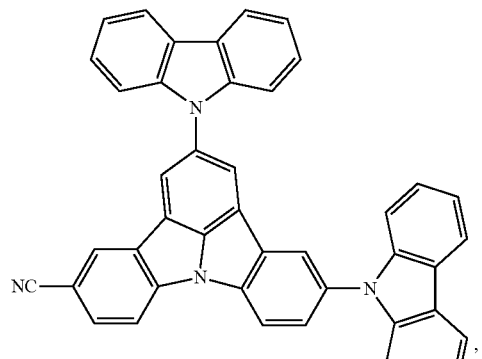

,

[Structural formula 13]

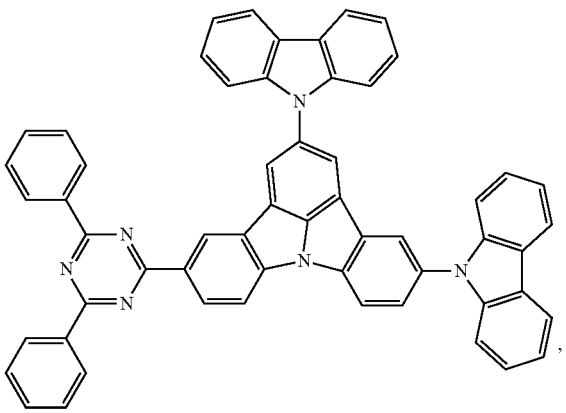

,

[Structural formula 14]

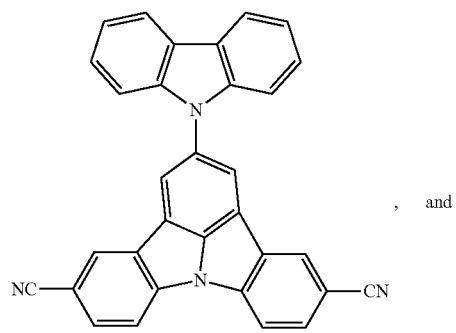

, and

[Structural formula 15]

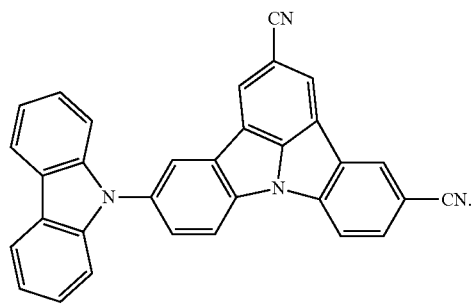

.

In a second aspect of the present disclosure, there is provided an organic light-emitting device including a light emission layer, wherein the layer contains any one of the delayed fluorescence material as above defined.

According to the present disclosure, various electron acceptor functional groups are bound to the indolocarbazole group as conventionally used as an electron donor unit, and, thus, the indolocarbazole group having the electron acceptor functional groups bound thereto acts as the electron acceptor unit for the delayed fluorescent material. Therefore, the delayed fluorescent material according to the embodiment of the present disclosure may realize high thermal stability, high luminous efficiency and improved electron transfer.

Further, in the conventional delayed fluorescent material, the number of the structures of the electron acceptor unit is limited, and thus there are many limitations in the molecular structure of the delayed fluorescent material. However, according to the present disclosure, a variety of molecular structures of the delayed fluorescent material may be achieved by using the indolocarbazole group having the electron acceptor functional groups bound thereto as the electron acceptor unit for the delayed fluorescent material.

BRIEF DESCRIPTION OF THE DRAWINGS

The accompanying drawings, which are incorporated in and form a part of this specification and in which like numerals depict like elements, illustrate embodiments of the present disclosure and, together with the description, serve to explain the principles of the disclosure.

Figure 1:
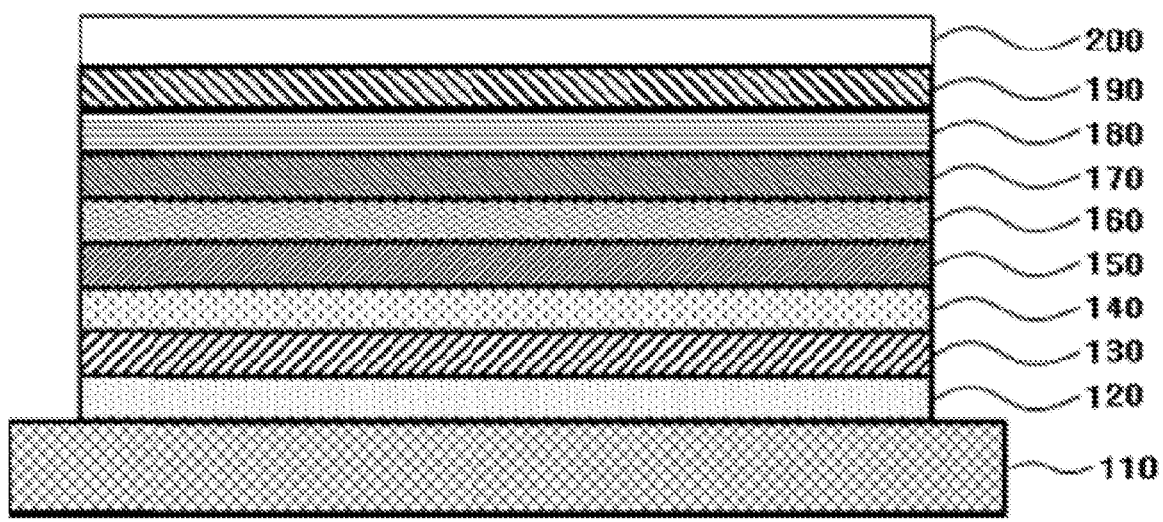
FIG. 1 is a cross-sectional view illustrating an organic light emitting device according to an embodiment of the present disclosure.

For simplicity and clarity of illustration, elements in the figures are not necessarily drawn to scale. The same reference numbers in different figures denote the same or similar elements, and as such perform similar functionality. Also, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

DETAILED DESCRIPTIONS

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Spatially relative terms, such as "beneath," "below," "lower," "under," "above," "upper," and the like, may be used herein for ease of explanation to describe one element or feature's relationship to another element s or feature s as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented for example, rotated 90 degrees or at other orientations, and the spatially relative descriptors used herein should be interpreted accordingly.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the following description, numerous specific details are set forth in order to provide a thorough understanding of the present disclosure. The present disclosure may be practiced without some or all of these specific details. In other instances, well-known process structures and/or processes have not been described in detail in order not to unnecessarily obscure the present disclosure.

The delayed fluorescence material according to an embodiment of the present disclosure includes a compound has a molecular structure comprising at least one electron donor unit configured to donate electrons and an electron acceptor unit coupled to the electron donor unit and configured to accept electrons. Thus, the compound with the molecular structure containing the electron donor unit and the electron acceptor unit has a small energy difference between the excited singlet energy and excited triplet energy. Thus, via the thermal energy, the excitons in the excited triplet state may be state-shifted to the excited singlet state, thereby exhibiting the retarded fluorescence property.

In one embodiment of the present disclosure, the electron acceptor unit includes an indolocarbazole group having at least one acceptor functional-group bound to the indolocarbazole group.

In one embodiment, the molecular structure has one of following structural formulas 1-1 to 1-6:

[Structural formula 1-1]

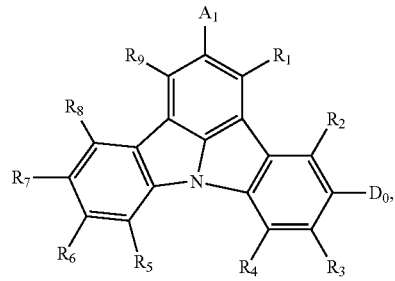

[Structural formula 1-2]

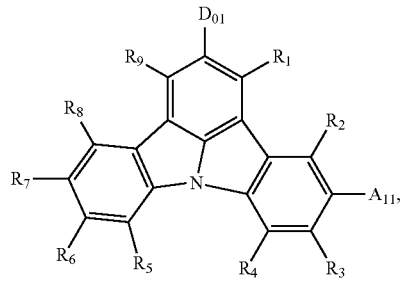

[Structural formula 1-3]

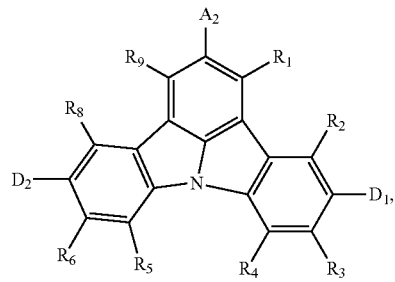

[Structural formula 1-4]

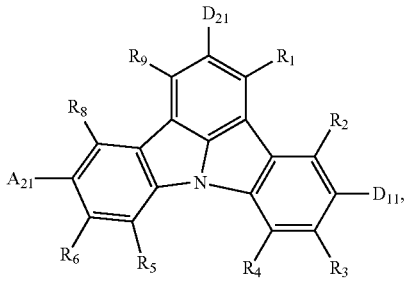

[Structural formula 1-5]

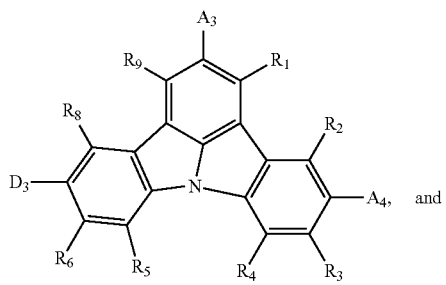

and

[Structural formula 1-6]

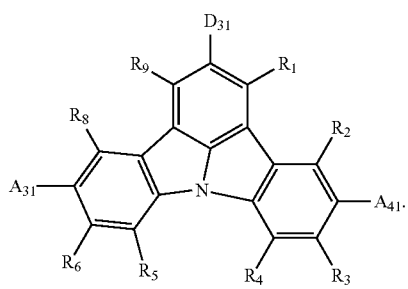

In the above structural formulas 1-1 to 1-6, each of $D_0$, $D_{01}$, $D_1$, $D_2$, $D_{11}$, $D_{21}$, $D_3$ and $D_{31}$ individually represents the electron donor unit, and each of $A_1$, $A_{11}$, $A_2$, $A_{21}$, $A_3$, $A_4$, $A_{31}$ and $A_{41}$ individually represents the acceptor functional-group.

In the above structural formulas 1-1 to 1-6, each of $R_1$ to $R_9$ individually represents one selected from a group consisting of hydrogen, deuterium, an alkyl group having 1 to 60 carbon atoms, an alkylthio group having 1 to 10 carbon atoms, an alkyl-substituted amino group having 1 to 10 carbon atoms, an aralkyl group having 7 to 20 carbon atoms, a diarylamino group having 12 to 24 carbon atoms, an alkoxycarbonyl group having 2 to 10 carbon atoms, an alkylsulfonyl group having 1 to 10 carbon atoms, a haloalkyl group having 1 to 10 carbon atoms, an amino group, an alkylamide group having 2 to 10 carbon atoms, a trialkylsilyl group having 3 to 20 carbon atoms, a trialkylsilylalkyl group having 4 to 20 carbon atoms, an alkenyl group having 2 to 60 carbon atoms, a trialkylsilylalkenyl group having 5 to 20 carbon atoms, an alkynyl group having 2 to 60 carbon atoms, a trialkylsilylalkynyl group having 5 to 20 carbon atoms, a cyano group, a nitro group, an aryl group having 6 to 60 carbon atoms, a heteroaryl group having 3 to 60 carbon atoms, an alkoxy group having 1 to 60 carbon atoms, an aryloxy group having 6 to 60 carbon atoms, an arylalkyl group having 7 to 60 carbon atoms, a heteroarylalkyl group having 3 to 60 carbon atoms, a cycloalkyl group having 3 to 60 carbon atoms, a heterocycloalkyl group having 1 to 60 carbon atoms, an alkylsilyl group having 3 to 60 carbon atoms, an arylsilyl group having 3 to 60 carbon atoms, a heteroarylsilyl group having 1 to 60 carbon atoms, and a substituted or unsubstituted aromatic 6-membered heterocycle having 3 to 30 carbon atoms. At least two of $R_1$ to $R_9$ may be the same or different. Adjacent two of $R_1$ to $R_9$ may be coupled to form a ring.

The electron donor unit is not particularly limited as long as the electron donor unit donates electrons to the electron acceptor unit to induce charge movement in the molecular structure including the above Structural formulas 1-1 to 1-6. In one embodiment, each of $D_0$, $D_{01}$, $D_1$, $D_2$, $D_{11}$, $D_{21}$, $D_3$ and $D_{31}$ individually includes a functional-group compound derived from one selected from a group consisting of compounds having following structural formulas 2-1 to 2-52 respectively:

[Structural formula 2-1]

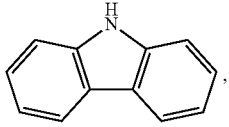

[Structural formula 2-2]

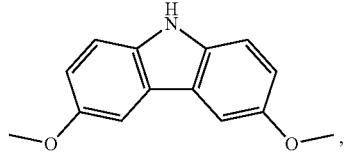

[Structural formula 2-3]

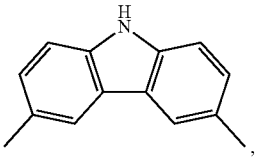

[Structural formula 2-4]

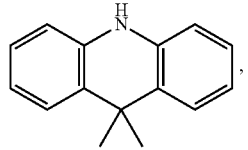

[Structural formula 2-5]

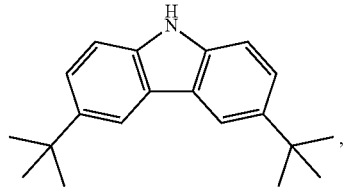

[Structural formula 2-6]

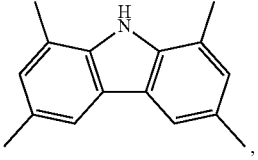

[Structural formula 2-7]

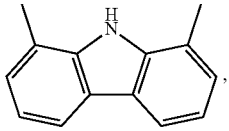

[Structural formula 2-8]

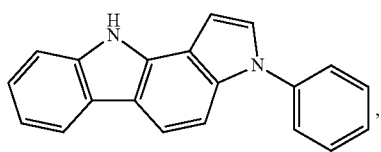

[Structural formula 2-9]
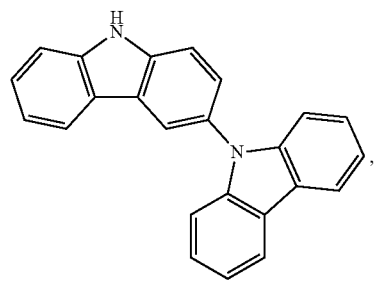
[Structural formula 2-10]
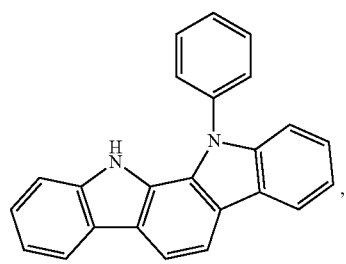
[Structural formula 2-11]
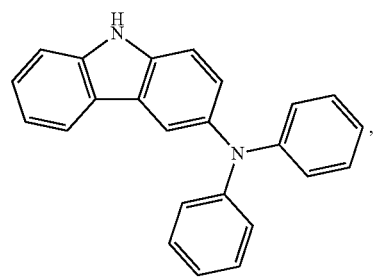
[Structural formula 2-12]
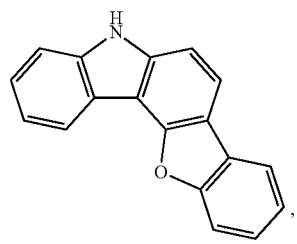
[Structural formula 2-13]
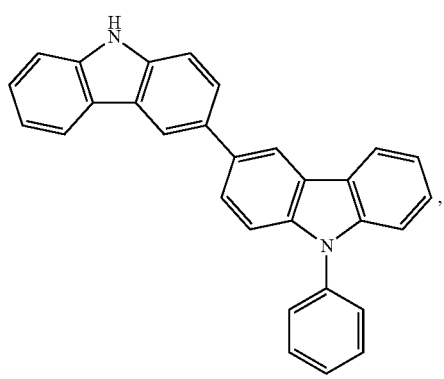
[Structural formula 2-14]
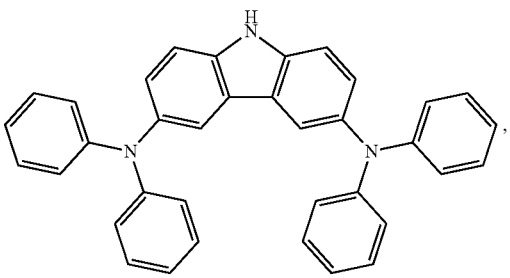
[Structural formula 2-15]
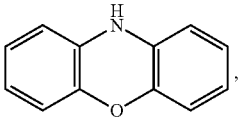
[Structural formula 2-16]
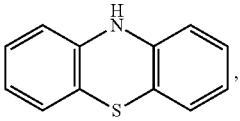
[Structural formula 2-17]
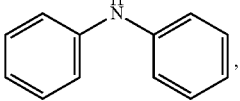
[Structural formula 2-18]
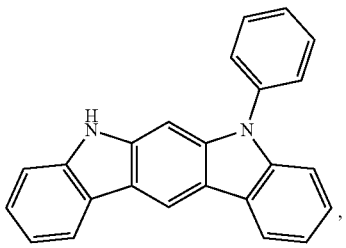
[Structural formula 2-19]
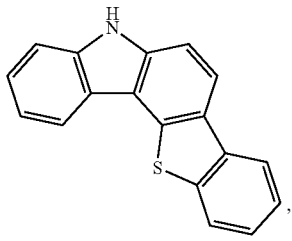
[Structural formula 2-20]
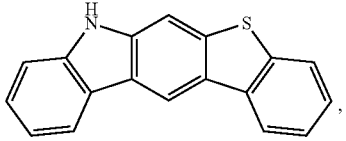
[Structural formula 2-21]
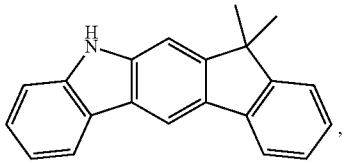

[Structural formula 2-22]
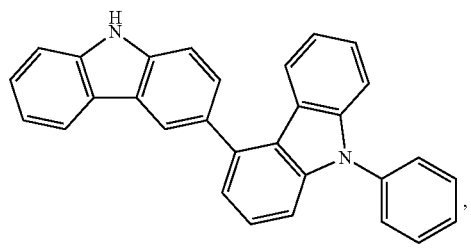
[Structural formula 2-23]
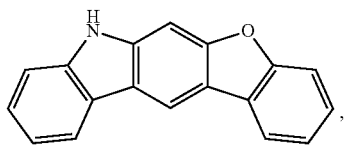
[Structural formula 2-24]
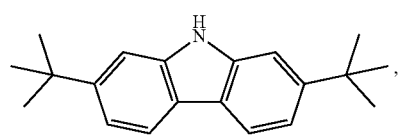
[Structural formula 2-25]
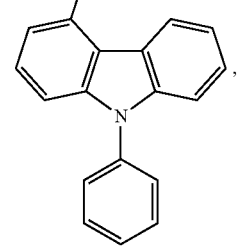
[Structural formula 2-26]
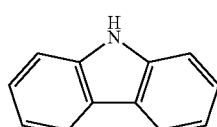
[Structural formula 2-27]
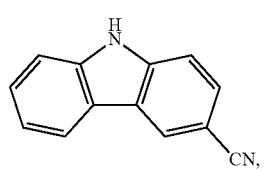
[Structural formula 2-28]
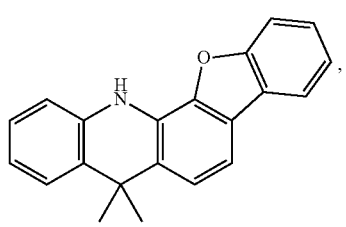
[Structural formula 2-29]
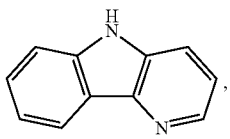
[Structural formula 2-30]
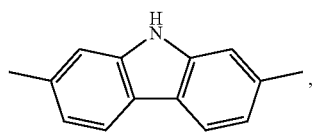
[Structural formula 2-31]
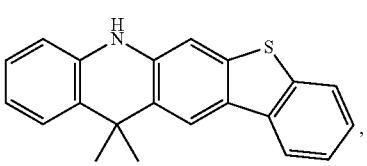
[Structural formula 2-32]
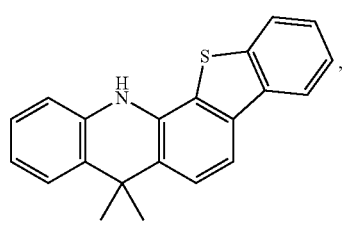
[Structural formula 2-33]
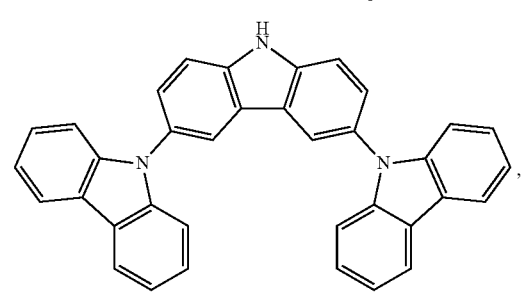
[Structural formula 2-34]
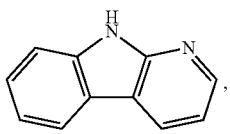
[Structural formula 2-35]
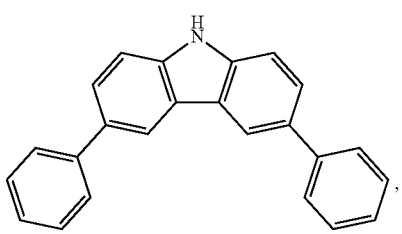
[Structural formula 2-36]
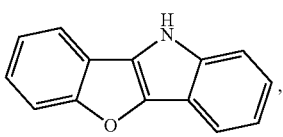

[Structural formula 2-37]
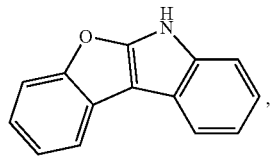
[Structural formula 2-38]
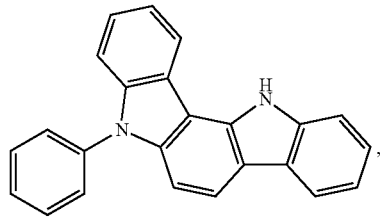
[Structural formula 2-39]
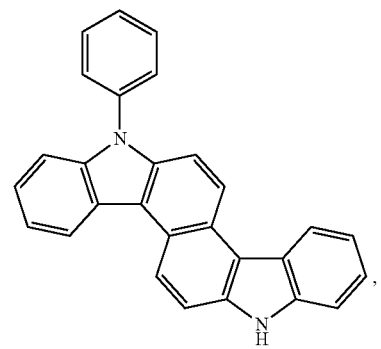
[Structural formula 2-40]
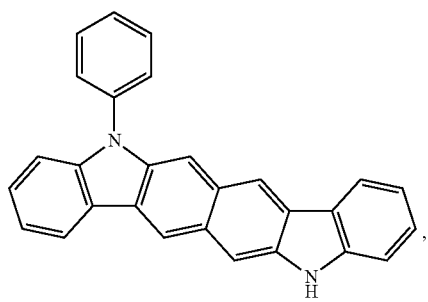
[Structural formula 2-41]
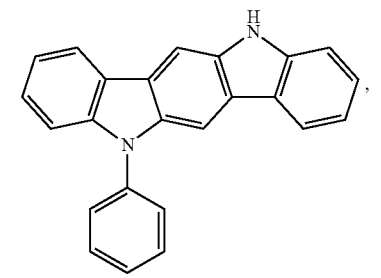
[Structural formula 2-42]
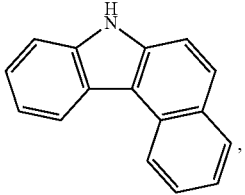
[Structural formula 2-43]
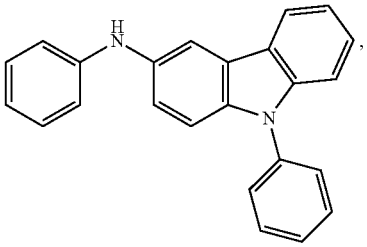
[Structural formula 2-44]
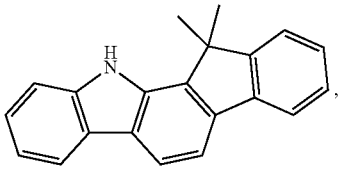
[Structural formula 2-45]
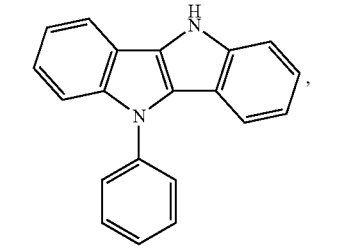
[Structural formula 2-46]
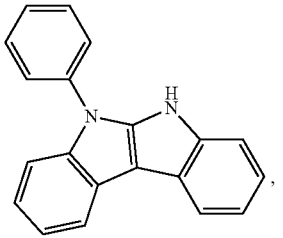
[Structural formula 2-47]
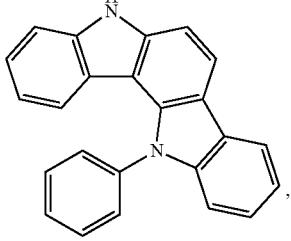
[Structural formula 2-48]
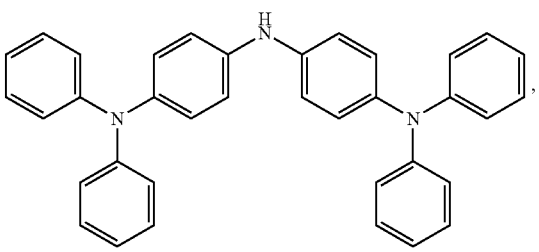
[Structural formula 2-49]
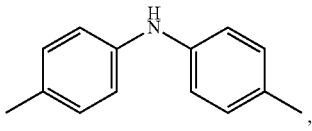

-continued

[Structural formula 2-50]

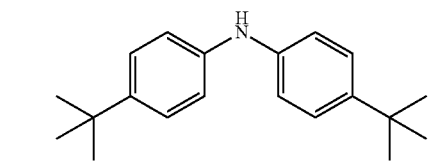

[Structural formula 2-51]

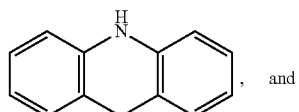
and

[Structural formula 2-52]

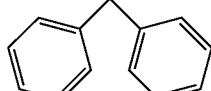

compound derived from one selected from a group consisting of compounds having following structural formulas 3-1 to 3-4 respectively:

[Structural formula 3-1]

C≡N,

[Structural formula 3-2]

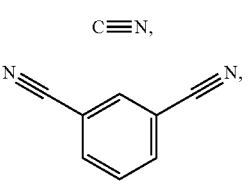

[Structural formula 3-3]

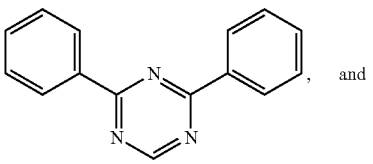
, and

[Structural formula 3-4]

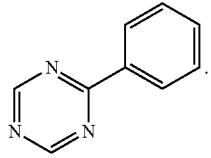

In one embodiment of the delayed fluorescent material, as the acceptor functional group, each of $A_1$, $A_{11}$, $A_2$, $A_{21}$, $A_3$, $A_4$, $A_{31}$ and $A_{41}$ individually includes a functional-group In one embodiment, the molecular structure of the delayed fluorescent material has one of following structural formulas 4 to 15:

[Structural formula 4]

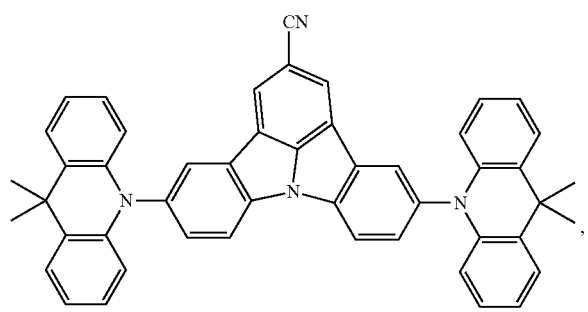

[Structural formula 5]

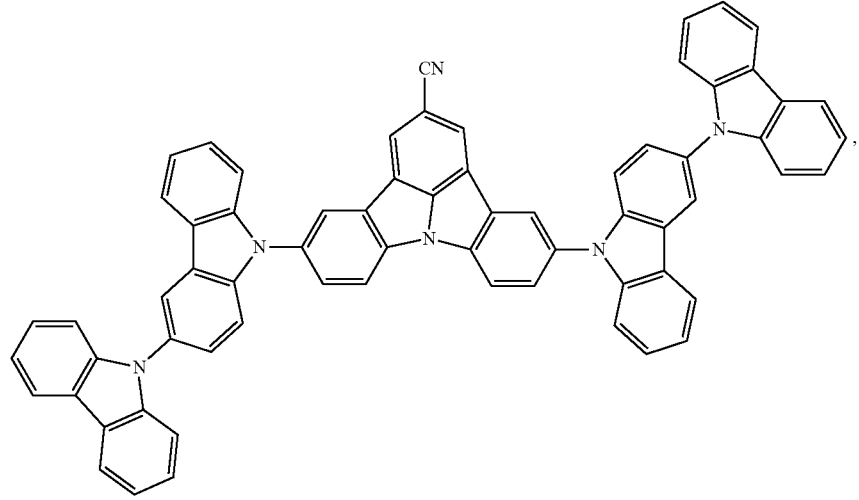

-continued
[Structural formula 6]
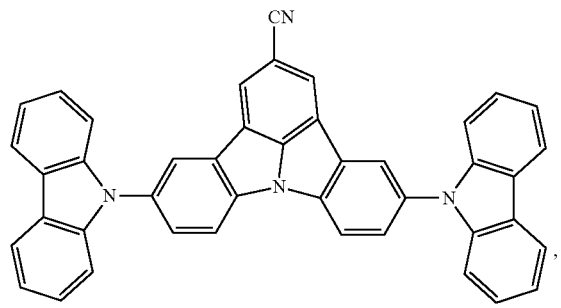
[Structural formula 7]
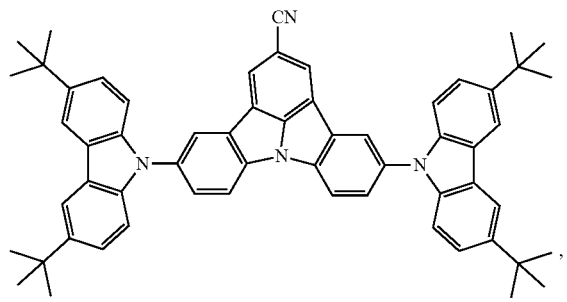
[Structural formula 8]
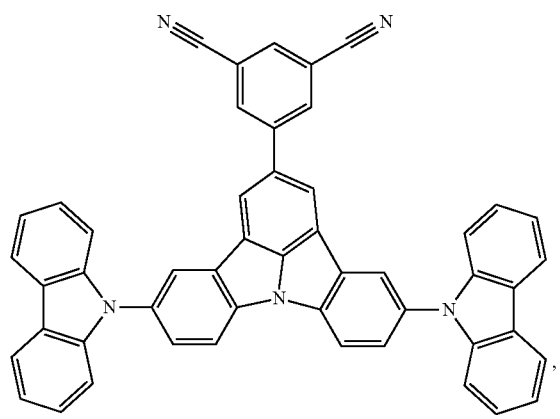
[Structural formula 9]
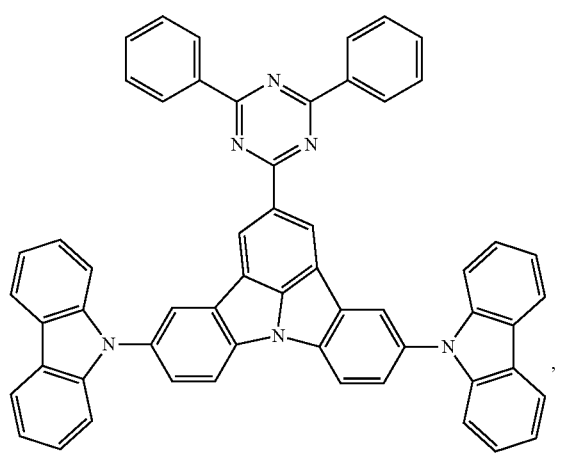
[Structural formula 10]
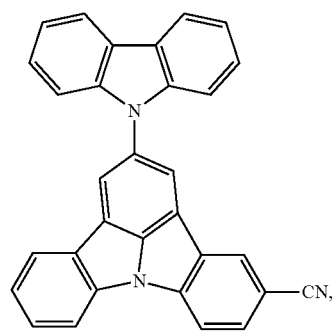
[Structural formula 11]
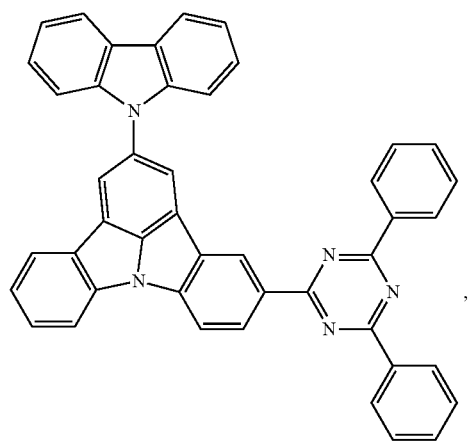

[Structural formula 12]

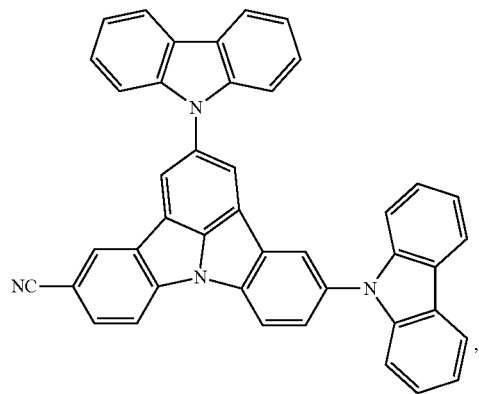

,

[Structural formula 13]

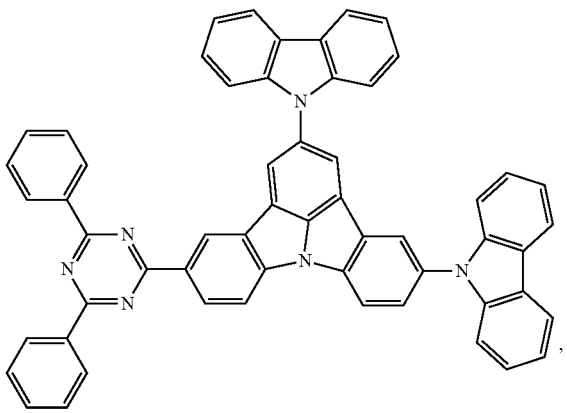

,

[Structural formula 14]

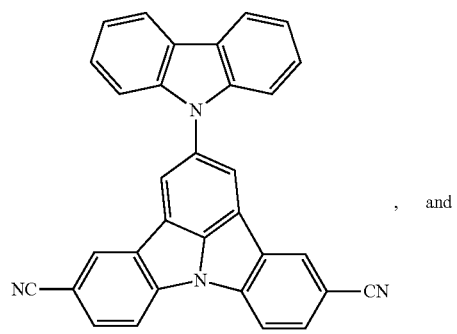

, and

[Structural formula 15]

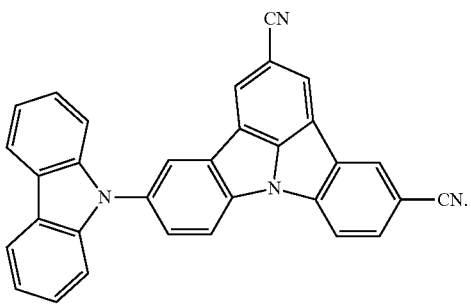

.

According to the present disclosure, the various electron acceptor functional groups are bound to the indolocarbazole group as conventionally used as an electron donor unit, and, thus, the indolocarbazole group having the electron acceptor functional groups bound thereto acts as the electron acceptor unit for the delayed fluorescent material. Therefore, the delayed fluorescent material according to the embodiment of the present disclosure may realize high thermal stability, high luminous efficiency and improved electron transfer.

Further, in the conventional delayed fluorescent material, the number of the structures of the electron acceptor unit is limited, and thus there are many limitations in the molecular structure of the delayed fluorescent material. However, according to the present disclosure, a variety of molecular structures of the delayed fluorescent material may be achieved by using the indolocarbazole group having the electron acceptor functional groups bound thereto as the electron acceptor unit for the delayed fluorescent material.

Below, a number of present examples are presented to help understand the present disclosure. The following present examples are intended merely to aid in the understanding of the present disclosure. Thus, the scope of the present disclosure is not limited to the present examples.

Present Example 1

According to a following chemical reaction 1, a delayed fluorescent material having a molecular structure of the above Structural formula 4 was synthesized:

[Chemical reaction 1]

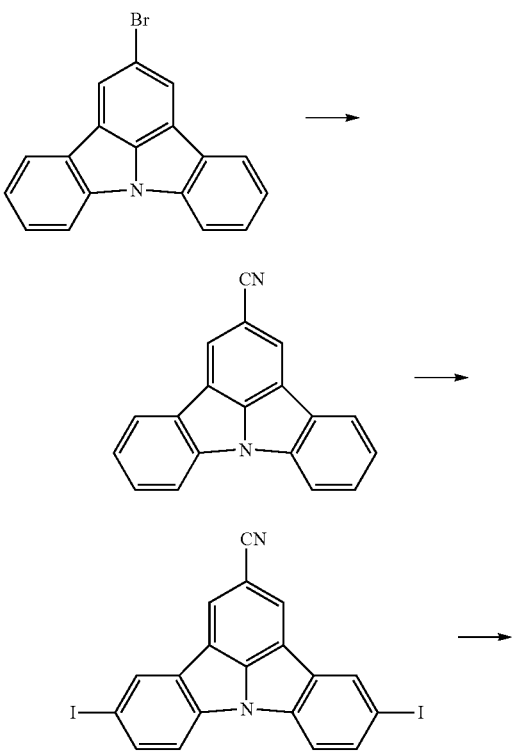

-continued

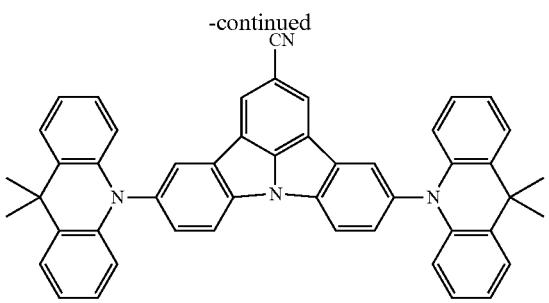

In detail, the delayed fluorescent material of Structural formula 4 was synthesized as follows.

Synthesis of Indolo[3,2,1-jk]carbazole-2-carbonitrile

A mixture of 2-bromoindolo[3,2,1-jk]carbazole (1 g, 3.12 mmol), CuCN (0.56 g, 6.24 mmol) were added to a pressure tube in DMF (10 ml). The reaction was heated to 150° C. for 24 h. the reaction mixture was cooled to room temperature. And then, the mixture was extracted with chloroform. The solvent was concentrated under vacuum and the product was isolated by column chromatography on a silica gel.

Synthesis of 5,11-diiodoindolo[3,2,1-jk]carbazole-2-carbonitrile

Indolo[3,2,1-jk]carbazole-2-carbonitrile (0.6 g, 2.25 mmol), periodic acid (1.03 g, 4.51 mmol) were dissolved in acetic acid (30 ml). And then, iodine (1.14 g, 4.5 mmol) was added to the solution. The reaction mixture was stirred at 60° C. for 30 min followed by addition of distilled water (0.6 ml) and sulfuric acid (0.06 ml). The solution was refluxed for 18 h, cooled to room temperature and poured into distilled water. The mixture was filtered and diluted with ethyl acetate and washed with distilled water and sodium thiosulfate. The organic layer was dried over anhydrous MgSO4 and evaporated in vacuo. The crude product was washed with hexane after drying in vacuum. Yellowish powder was obtained after drying in vacuum. The product was included 85% of all powder and it was confirmed by HPLC analysis. The synthesized 5,11-diiodoindolo[3,2,1-jk]carbazole-2-carbonitrile was used in the next reaction without further purification.

[Synthesis of a Compound of Structural Formula 4]

5,11-diiodoindolo[3,2,1-jk]carbazole-2-carbonitrile (0.5 g, 0.97 mmol), 9,9-dimethyl-9,10-dihydroacridine (0.44 g, 2.12 mmol) and sodium tert-butoxide (0.04 g, 0.39 mmol) were dissolved in toluene (50 ml) under N2 bubbling for 30 min. Pd2(dba)3 (0.36, 0.39 mmol) and tri-tert-butylphosphine (0.08 g, 0.39 mmol) were added in the mixture and the reaction mixture was refluxed overnight. After cooling to room temperature, the mixture was filtered and diluted with ethyl acetate and washed with distilled water. The organic layer was dried over anhydrous MgSO4 and evaporated in vacuum. The mixture was purified by vacuum sublimation to obtain yellowish white powder.

Present Example 2

According to a following chemical reaction 2, a delayed fluorescent material having a molecular structure of the above Structural formula 5 was synthesized:

[Chemical reaction 2]

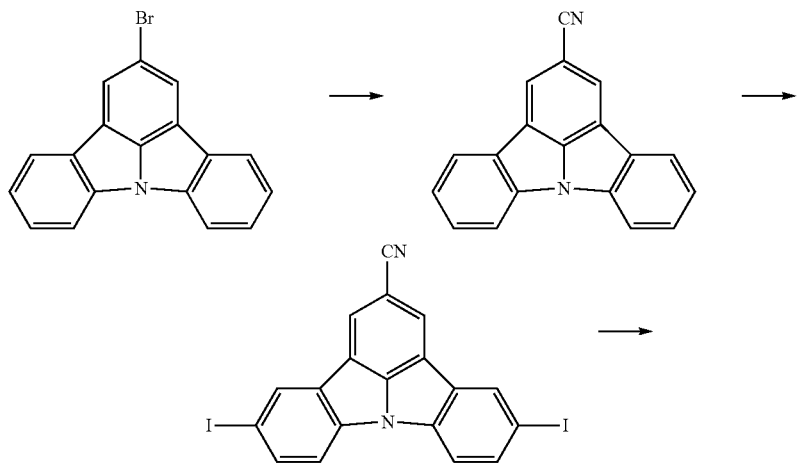

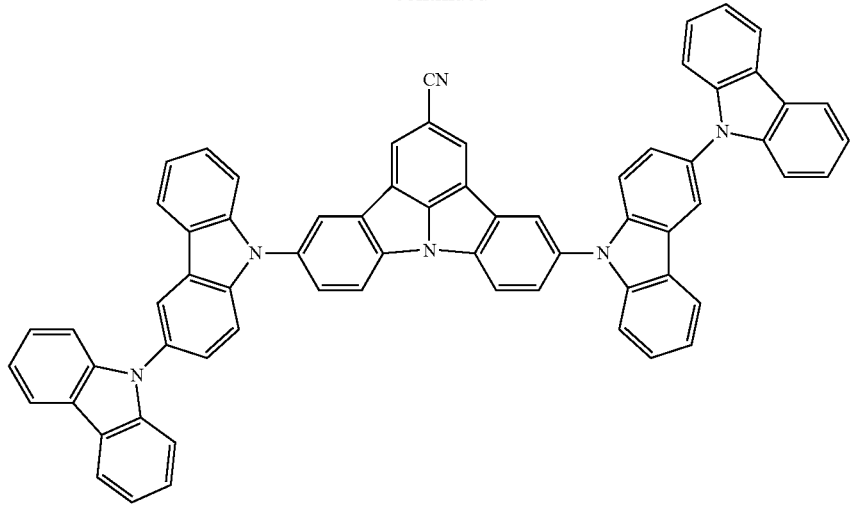

In detail, 5,11-diiodoindolo[3,2,1-jk]carbazole-2-carbonitrile (1.36 g, 2.63 mmol), 9H-3,9'-bicarbazole (1.92 g, 5.77 mmol), K3PO4 (2.23 g, 10.5 mmol) and CuI (0.5 g, 2.63 mmol) were dissolved in DMF (100 ml) under a nitrogen atmosphere. The reaction mixture was stirred with N2 bubbling for 30 min and trans-1,2-DCH (0.3 g, 2.63 mmol) was added to the solution followed by reflux overnight. After cooling to room temperature, the mixture was filtered and diluted with methylene chloride and washed with distilled water. The organic layer was dried over anhydrous MgSO4 and evaporated in vacuum. The mixture was purified repeatedly by vacuum sublimation to obtain yellow powder.

Present Example 3

According to a following chemical reaction 3, a delayed fluorescent material having a molecular structure of the above Structural formula 6 was synthesized:

[Chemical Reaction 3]

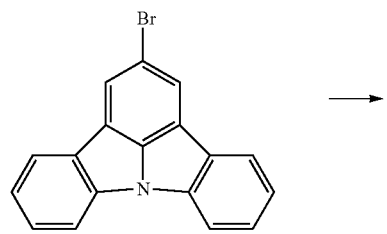

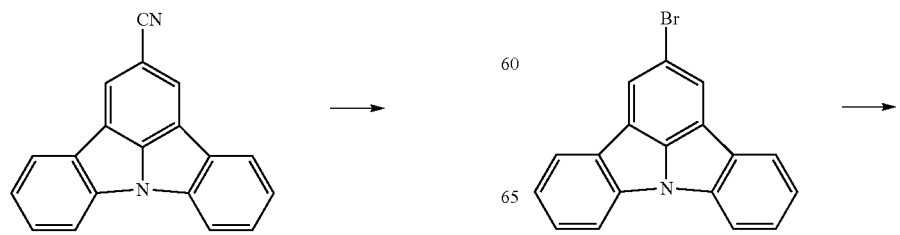

In detail, the delayed fluorescent material of Structural formula 6 was synthesized according to the present example 2, using carbazole instead of 9H-3,9'-bicarbazole.

Present Example 4

According to a following chemical reaction 4, a delayed fluorescent material having a molecular structure of the above Structural formula 7 was synthesized:

[Chemical reaction 4]

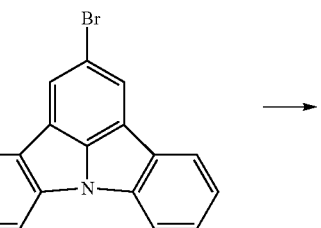

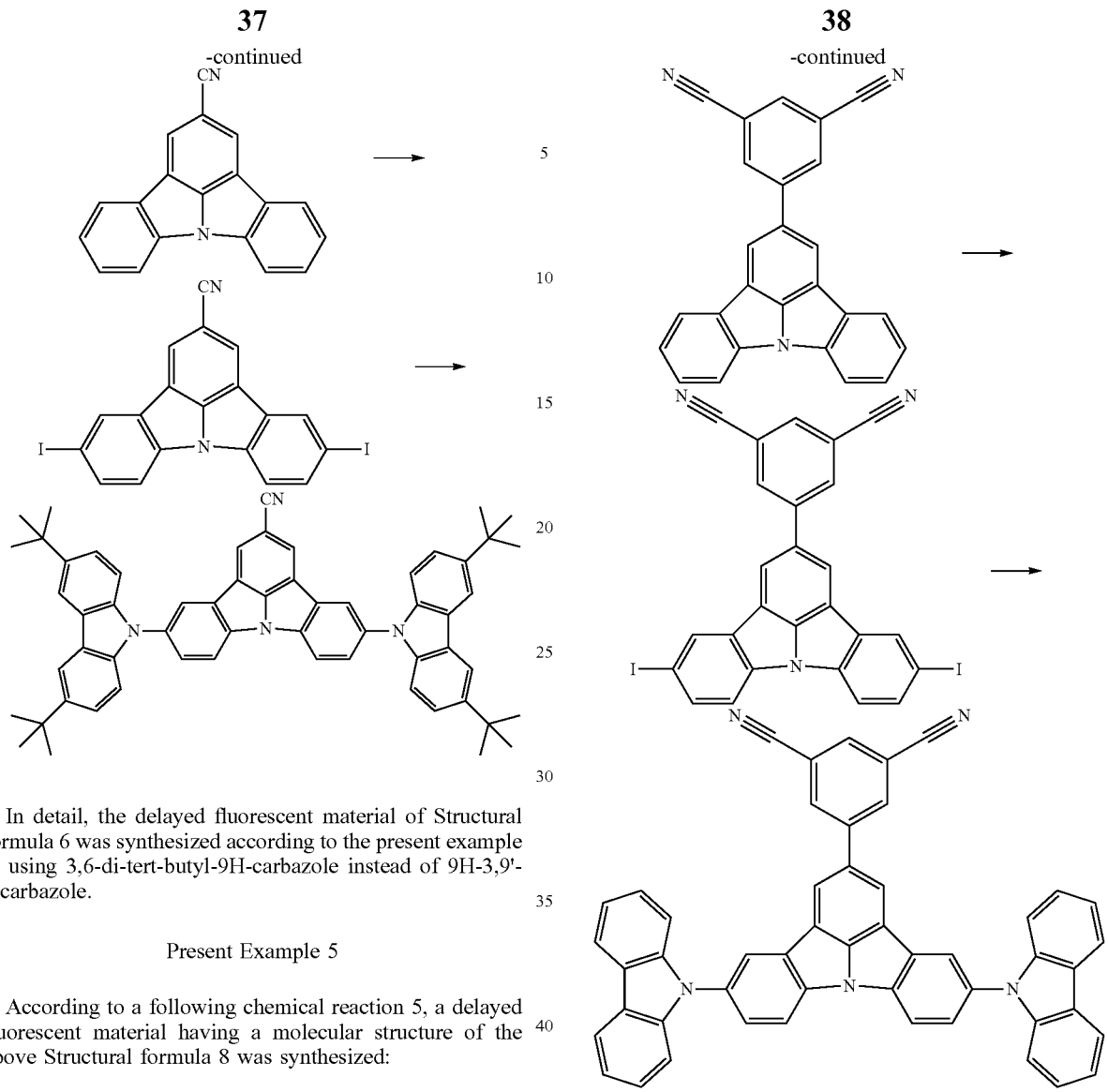

In detail, the delayed fluorescent material of Structural formula 6 was synthesized according to the present example 2, using 3,6-di-tert-butyl-9H-carbazole instead of 9H-3,9'-bicarbazole.

Present Example 5

According to a following chemical reaction 5, a delayed fluorescent material having a molecular structure of the above Structural formula 8 was synthesized:

[Chemical reaction 5]

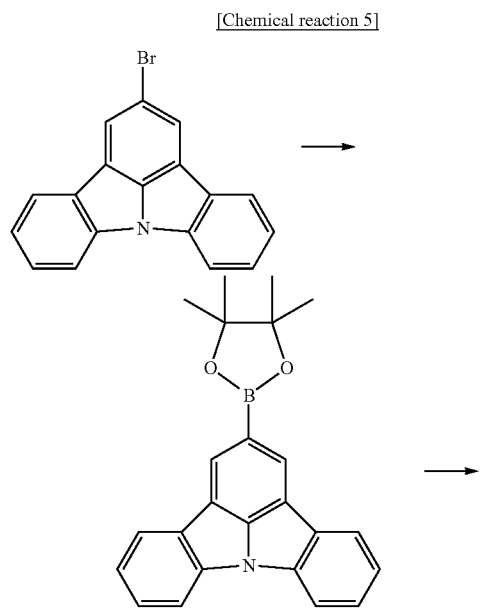

In detail, the delayed fluorescent material of Structural formula 8 was synthesized as follows.

Synthesis of 2-(4,4,5,5-tetramethyl-1,3,2-dioxaborolan-2-yl)indolo[3,2,1-jk]carbazole 2-bromoindolo[3,2,1-jk]carbazole (5 g, 15.6 mmol), 4,4,4',4',5,5,5',5'-octamethyl-2,2'-bi(1,3,2-dioxaborolane) (7.9 g, 31.2 mmol), Pd(OAc)$_2$ (0.35 g, 1.56 mmol), X-phos (1.48 g, 3.12 mmol) and KOAc (4.59 g, 46.82 mmol) were dissolved in 1,4-dioxane (275 ml) under a nitrogen atmosphere. The reaction mixture was stirred with N2 bubbling for 30 min and refluxed overnight. After cooling to room temperature, the mixture was filtered and diluted with methylene chloride and washed with distilled water. The organic layer was dried over anhydrous MgSO4 and evaporated in vacuum. And then, the product was isolated by column chromatography on a silica gel.

Synthesis of 5-(indolo[3,2,1-jk]carbazol-2-yl)isophthalonitrile 5-bromoisophthalonitrile (1 g, 48.3 mmol), 2-(4,4,5,5-tetramethyl-1,3,2-dioxaborolan-2-yl)indolo[3,2,1-jk]carbazole (1.77 g, 48.3 mmol) were dissolved in 1,4dioxane (50 ml). $K_2CO_3$ (1.34 g, 96.6 mmol) was dissolved in water and poured into the mixture. The reaction mixture was stirred with N2 bubbling for 30 min and refluxed overnight. After cooling to room temperature, the mixture was filtered and diluted with methylene chloride and washed with distilled water. The organic layer was dried over anhydrous $MgSO_4$ and evaporated in vacuum. And then, the product was isolated by column chromatography on a silica gel.

Synthesis of 5-(5,11-diiodoindolo[3,2,1-jk]carbazol-2-yl)isophthalonitrile

It was synthesized according to the previous method (refer to Present example 1 above).

[Synthesis of the Delayed Fluorescent Material of Structural Formula 8]

It was synthesized according to the previous method (refer to Present example 2 above).

Present Example 6

According to a following chemical reaction 6, a delayed fluorescent material having a molecular structure of the above Structural formula 9 was synthesized:

[Chemical reaction 6]

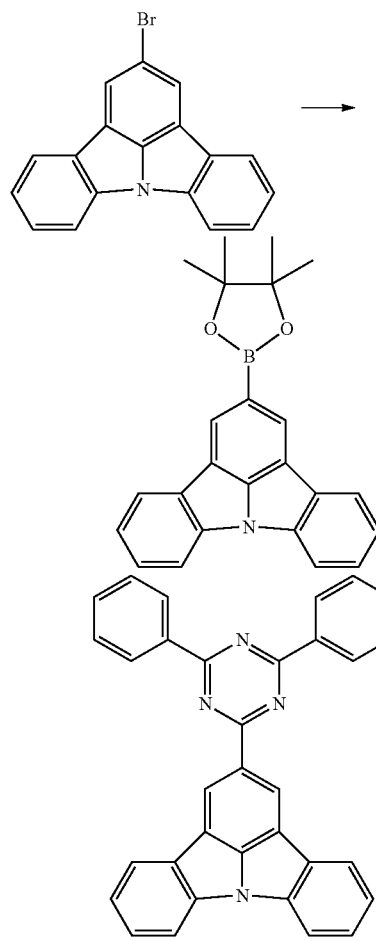

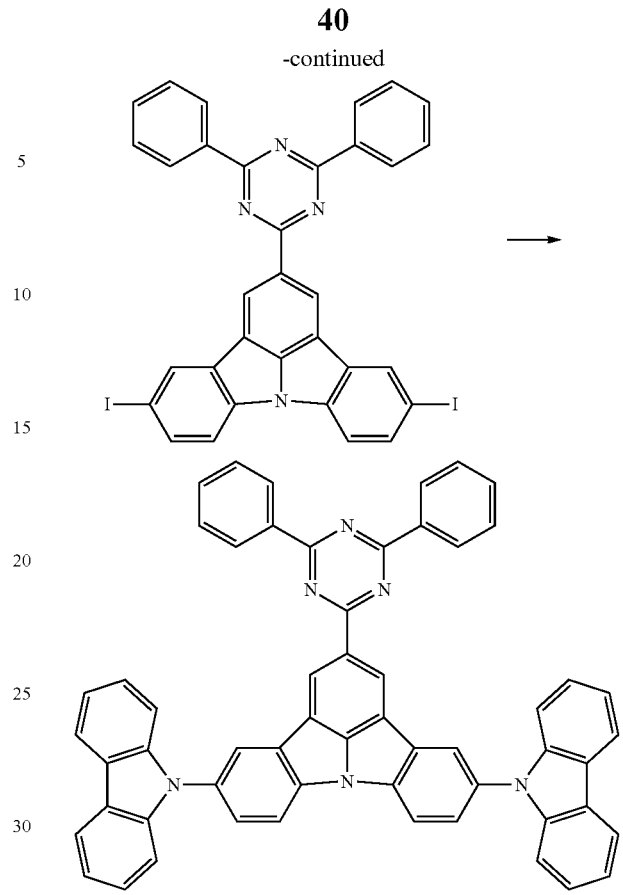

In detail, the delayed fluorescent material of Structural formula 9 was synthesized according to the Present example 6, using 2-chloro-4,6-diphenyl-1,3,5-triazine instead of 5-bromoisophthalonitrile.

Present Example 7

According to a following chemical reaction 7, a delayed fluorescent material having a molecular structure of the above Structural formula 10 was synthesized:

[Chemical reaction 7]

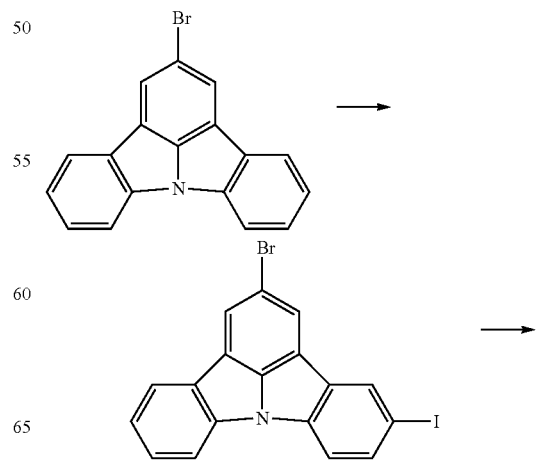

-continued

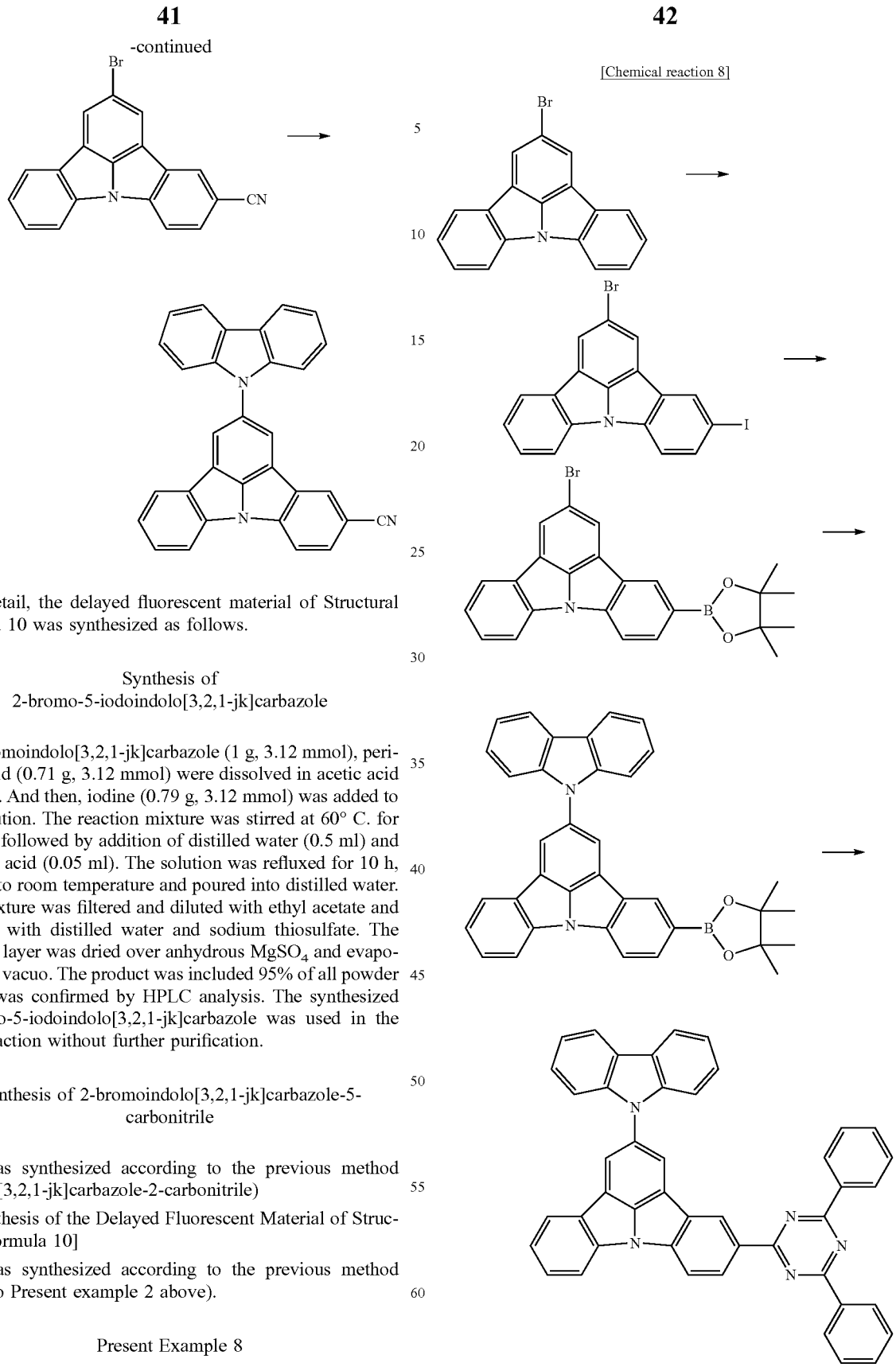

In detail, the delayed fluorescent material of Structural formula 10 was synthesized as follows.

Synthesis of
2-bromo-5-iodoindolo[3,2,1-jk]carbazole 2-bromoindolo[3,2,1-jk]carbazole (1 g, 3.12 mmol), periodic acid (0.71 g, 3.12 mmol) were dissolved in acetic acid (50 ml). And then, iodine (0.79 g, 3.12 mmol) was added to the solution. The reaction mixture was stirred at 60° C. for 30 min followed by addition of distilled water (0.5 ml) and sulfuric acid (0.05 ml). The solution was refluxed for 10 h, cooled to room temperature and poured into distilled water. The mixture was filtered and diluted with ethyl acetate and washed with distilled water and sodium thiosulfate. The organic layer was dried over anhydrous MgSO$_4$ and evaporated in vacuo. The product was included 95% of all powder and it was confirmed by HPLC analysis. The synthesized 2-bromo-5-iodoindolo[3,2,1-jk]carbazole was used in the next reaction without further purification.

Synthesis of 2-bromoindolo[3,2,1-jk]carbazole-5-carbonitrile

It was synthesized according to the previous method (Indolo[3,2,1-jk]carbazole-2-carbonitrile)

[Synthesis of the Delayed Fluorescent Material of Structural Formula 10]

It was synthesized according to the previous method (refer to Present example 2 above).

Present Example 8

According to a following chemical reaction 8, a delayed fluorescent material having a molecular structure of the above Structural formula 11 was synthesized:

[Chemical reaction 8]

In detail, the delayed fluorescent material of Structural formula 11 was synthesized as follows.

Synthesis of 2-bromo-5-(4,4,5,5-tetramethyl-1,3,2-dioxaborolan-2-yl)indolo[3,2,1-jk]carbazole It was synthesized according to the previous method (2-(4,4,5,5-tetramethyl-1,3,2-dioxaborolan-2-yl)indolo[3,2,1-jk]carbazole).

Synthesis of 2-(9H-carbazol-9-yl)-5-(4,4,5,5-tetramethyl-1,3,2-dioxaborolan-2-yl)indolo[3,2,1-jk]carbazole It was synthesized according to the previous method (refer to Present example 5 above).

[Synthesis of the Delayed Fluorescent Material of Structural Formula 11]

It was synthesized according to the previous method (refer to Present example 5 above)

Present Example 9

According to a following chemical reaction 9, a delayed fluorescent material having a molecular structure of the above Structural formula 12 was synthesized:

[Chemical reaction 9]

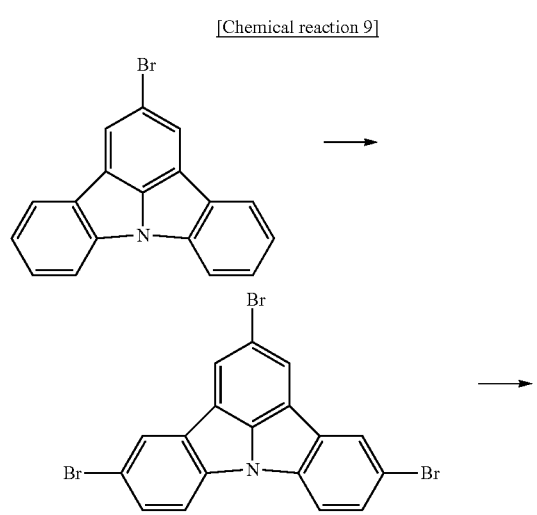

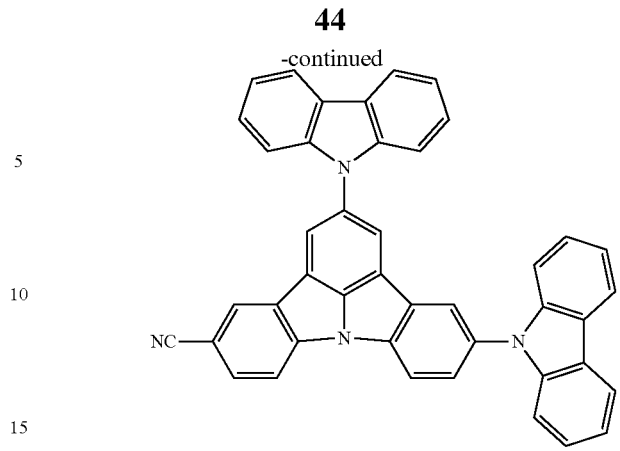

In detail, the delayed fluorescent material of Structural formula 12 was synthesized as follows.

Synthesis of 2,5,11-tribromoindolo[3,2,1-jk]carbazole

A solution of N-bromosuccinimide (3.5 g, 19.68 mmol) in 50 mL DMF was slowly added with stirring to a solution of 2-bromoindolo[3,2,1-jk]carbazole (3 g, 9.37 mmol) in 20 mL DMF with ice bath. After reacting for 2 h, the reaction mixture was poured into 600 mL ice water, and the crude product was collected by filtration to give white powder.

Synthesis of 5-bromo-2,11-di(9H-carbazol-9-yl)indolo[3,2,1-jk]carbazole

It was synthesized according to the previous method (compound 5).

[Synthesis of the Delayed Fluorescent Material of Structural Formula 12]

It was synthesized according to the previous method (Indolo[3,2,1-jk]carbazole-2-carbonitrile).

Present Example 10

According to a following chemical reaction 10, a delayed fluorescent material having a molecular structure of the above Structural formula 13 was synthesized:

[Chemical reaction 10]

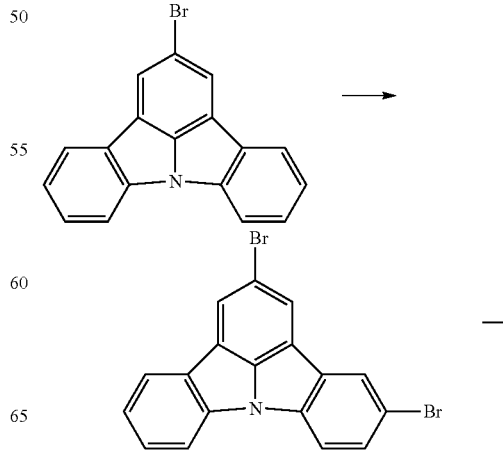

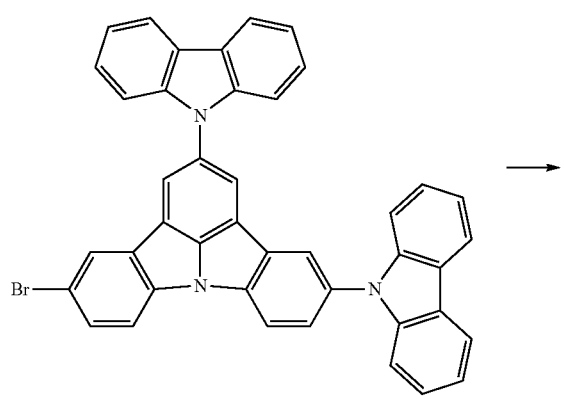

-continued

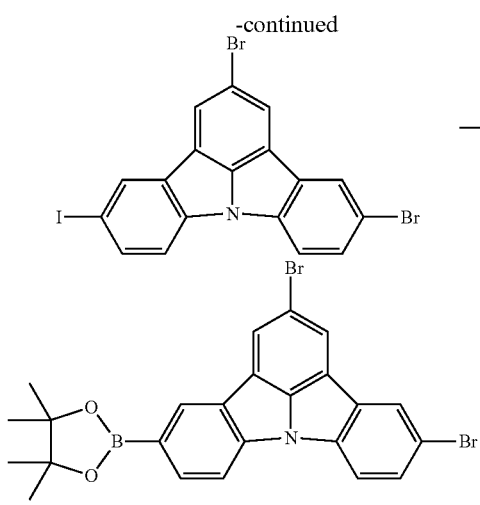

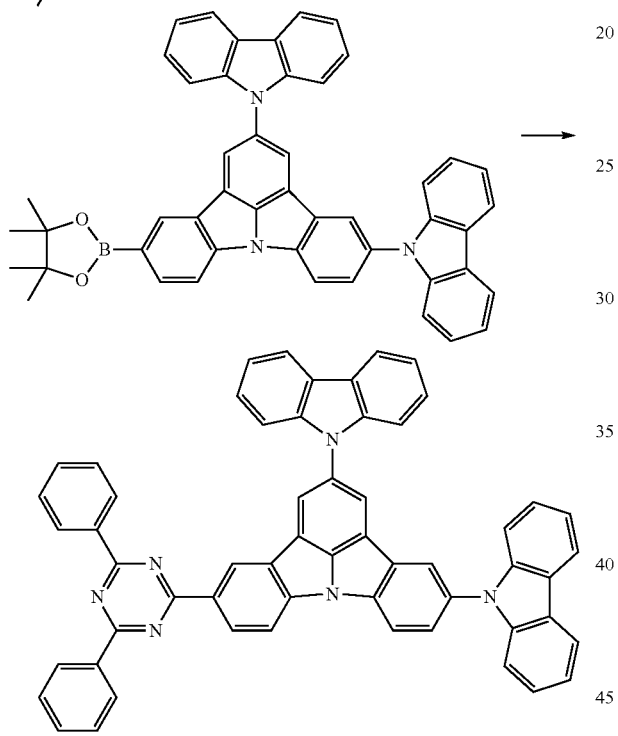

In detail, the delayed fluorescent material of Structural formula 13 was synthesized as follows.

Synthesis of 2,5-dibromoindolo[3,2,1-jk]carbazole

It was synthesized according to the previous method (2,5,11-tribromoindolo[3,2,1-jk]carbazole).

Synthesis of 2,5-dibromo-11-iodoindolo[3,2,1-jk]carbazole

It was synthesized according to the previous method (2-bromo-5-iodoindolo[3,2,1-jk]carbazole).

Synthesis of 2,5-dibromo-11-(4,4,5,5-tetramethyl-1,3,2-dioxaborolan-2-yl)indolo[3,2,1-jk]carbazole It was synthesized according to the previous method (2-(4,4,5,5-tetramethyl-1,3,2-dioxaborolan-2-yl)indolo[3,2,1-jk]carbazole).

Synthesis of 2,5-di(9H-carbazol-9-yl)-11-(4,4,5,5-tetramethyl-1,3,2-dioxaborolan-2-yl)indolo[3,2,1-jk]carbazole It was synthesized according to the previous method (refer to Present example 2 above)

[Synthesis of the Delayed Fluorescent Material of Structural Formula 13]

It was synthesized according to the previous method (refer to Present example 5 above)

Present Example 11

According to a following chemical reaction 11, a delayed fluorescent material having a molecular structure of the above Structural formula 14 was synthesized:

[Chemical reaction 11]

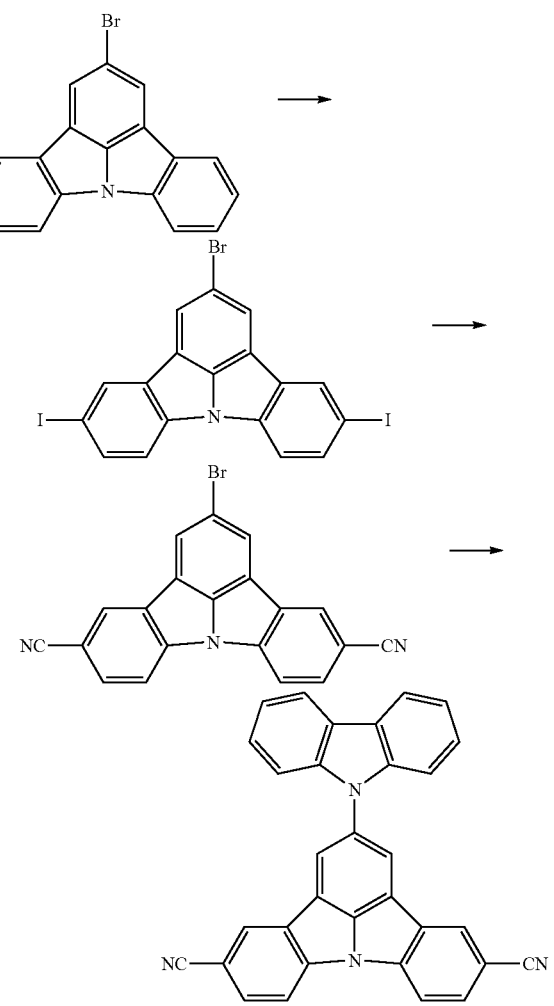

In detail, the delayed fluorescent material of Structural formula 14 was synthesized as follows.

Synthesis of 2-bromo-5,11-diiodoindolo[3,2,1-jk]carbazole

It was synthesized according to the previous method (2-bromo-5-iodoindolo[3,2,1-jk]carbazole).

Synthesis of 2-bromoindolo[3,2,1-jk]carbazole-5,11-dicarbonitrile

It was synthesized according to the previous method (Indolo[3,2,1-jk]carbazole-2-carbonitrile).

[Synthesis of the Delayed Fluorescent Material of Structural Formula 14]

It was synthesized according to the previous method (refer to Present example 2 above).

Present Example 12

According to a following chemical reaction 12, a delayed fluorescent material having a molecular structure of the above Structural formula 15 was synthesized:

[Chemical reaction 12]

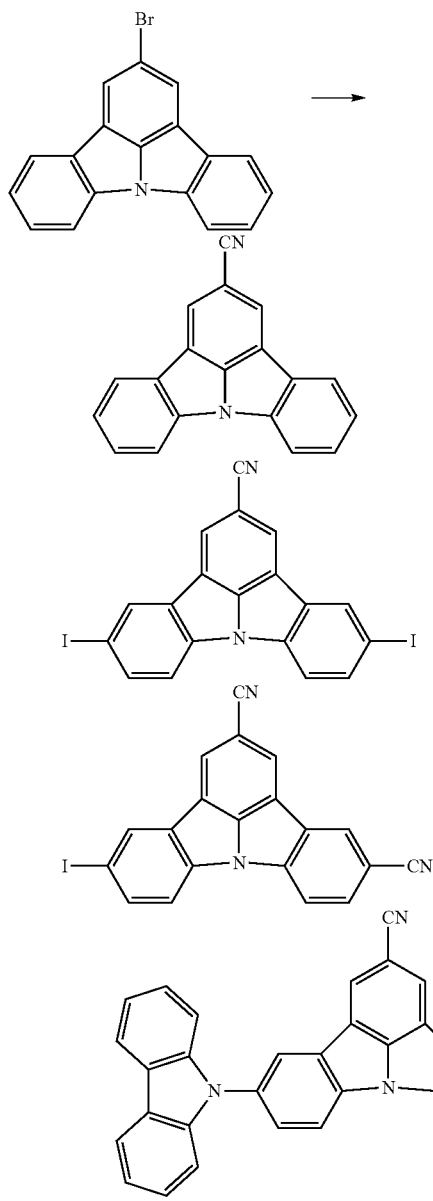

In detail, the delayed fluorescent material of Structural formula 15 was synthesized as follows.

Synthesis of indolo[3,2,1-jk]carbazole-2-carbonitrile

It was synthesized according to the previous method (Indolo[3,2,1-jk]carbazole-2-carbonitrile).

Synthesis of 5,11-diiodoindolo[3,2,1-jk]carbazole-2-carbonitrile

It was synthesized according to the previous method (2-bromo-5-iodoindolo[3,2,1-jk]carbazole).

Synthesis of 11-iodoindolo[3,2,1-jk]carbazole-2,5-dicarbonitrile

It was synthesized according to the previous method (Indolo[3,2,1-jk]carbazole-2-carbonitrile).

[Synthesis of the Delayed Fluorescent Material of Structural Formula 15]

It was synthesized according to the previous method (refer to Present example 2 above).

Comparative Example

According to a following chemical reaction 13, a delayed fluorescent material having a molecular structure of a following Structural formula 15 was synthesized:

[Chemical reaction 13]

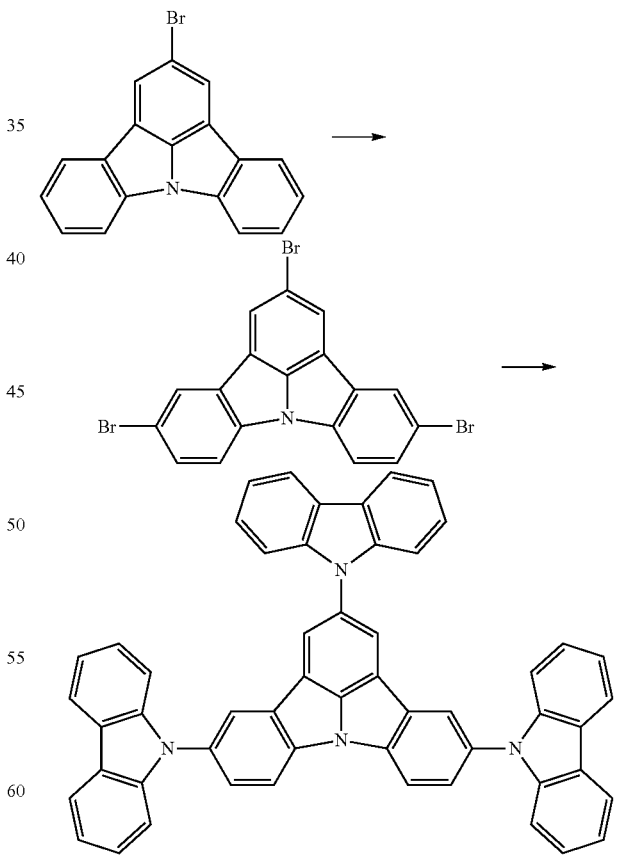

Structural formula 16

In detail, the delayed fluorescent material of Structural formula 15 was synthesized as follows Synthesis of
2,5,11-tribromoindolo[3,2,1-jk]carbazole It was synthesized according to the previous method (2,5,11-tribromoindolo[3,2,1-jk]carbazole).

[Synthesis of the Delayed Fluorescent Material of Structural Formula 16]

It was synthesized according to the previous method (compound 5).

Experimental Example

Delayed fluorescent materials synthesized according to the present example 1 to present example 12 and the comparative example as described above were used as dopant materials into the light-emission layers, respectively. Thus, the organic light-emitting devices 100 having the structure shown in FIG. 1 were fabricated. For convenience of illustration, the organic light-emitting devices fabricated using the delayed fluorescent materials synthesized according to the above defined present example 1 to present example 12 as the dopant materials into the light-emission layers thereof respectively will be referred to as first to twelfth organic light-emission devices respectively. The organic light-emitting device manufactured using the delayed fluorescent material synthesized according to the above-mentioned comparative example as the dopant material into the light-emission layer thereof is referred to as a 13-th organic light-emission device.

Each of the first to thirteenth organic light-emitting devices 100 includes a substrate 110, an anode 120, a hole injection layer 130, a hole transport layer 140, an exciton blocking layer 150, a light emitting layer 160, a hole blocking layer 170, an electron transport layer 180, an electron injection layer 190, and a cathode 200. These components were sequentially deposited using a vacuum deposition process.

The anode 120, the hole injection layer 130, the hole transport layer 140, the electron transport layer 180, the electron injection layer 190 and the cathode 200 may be respectively made of ITO (120), PEDOT:PSS(poly(3,4-ethylenedioxythiophene);poly(styrenesulfonate)) (130), TAPC(4,4'-cyclohexylidenebis[N,N-bis(4-methylphenyl) aniline]) (140), TPBi(1,3,5-tris(N-phenylbenzimidazole-2-yl)benzene) (180), LiF (190), and Al (200). The hole blocking layer 170 may be formed by depositing TSPO1(diphenyl (4-(triphenylsilyl)phenyl)phosphine oxide) on the light-emission layer 160. The exciton blocking layer 150 may be formed by depositing mCP(1,3-bis(N-carbazolyl)benzene) on the hole transport layer 140.

The light-emission layer 160 of each of the first to twelfth organic light-emitting devices was formed by doping, by 10%, each of the delayed fluorescent materials synthesized according to the present example 1 to present example 12 into DPEPO(Bis[2-(diphenylphosphino(phenyl]ether oxide) as a host material. The light-emission layer 160 of the thirteenth organic light-emitting devices was formed by doping, by 10%, each of the delayed fluorescent materials synthesized according to the comparative example into DPEPO(Bis[2-(diphenylphosphino(phenyl]ether oxide) as a host material.

The first to twelfth organic light-emitting devices fabricated using the delayed fluorescent materials synthesized according to the present examples 1 to 12 as the dopant materials for the light-emission layers thereof respectively exhibited quantum efficiencies expressed as delayed fluorescence emissions of blue color light of 17.3%, 13.2%, 12.4%, 16.0%, 12.2%, 13.6%, 12.1%, 13.4%, 11.8%, 12.9%, 15.1% and 14.8%, respectively.

On the contrary, the thirteenth organic light-emitting device fabricated using the delayed fluorescent material synthesized according to the comparative example as the dopant material for the light-emission layer thereof respectively exhibited quantum efficiency expressed as delayed fluorescence emission of blue color light of 2.3%.

Figure 2:
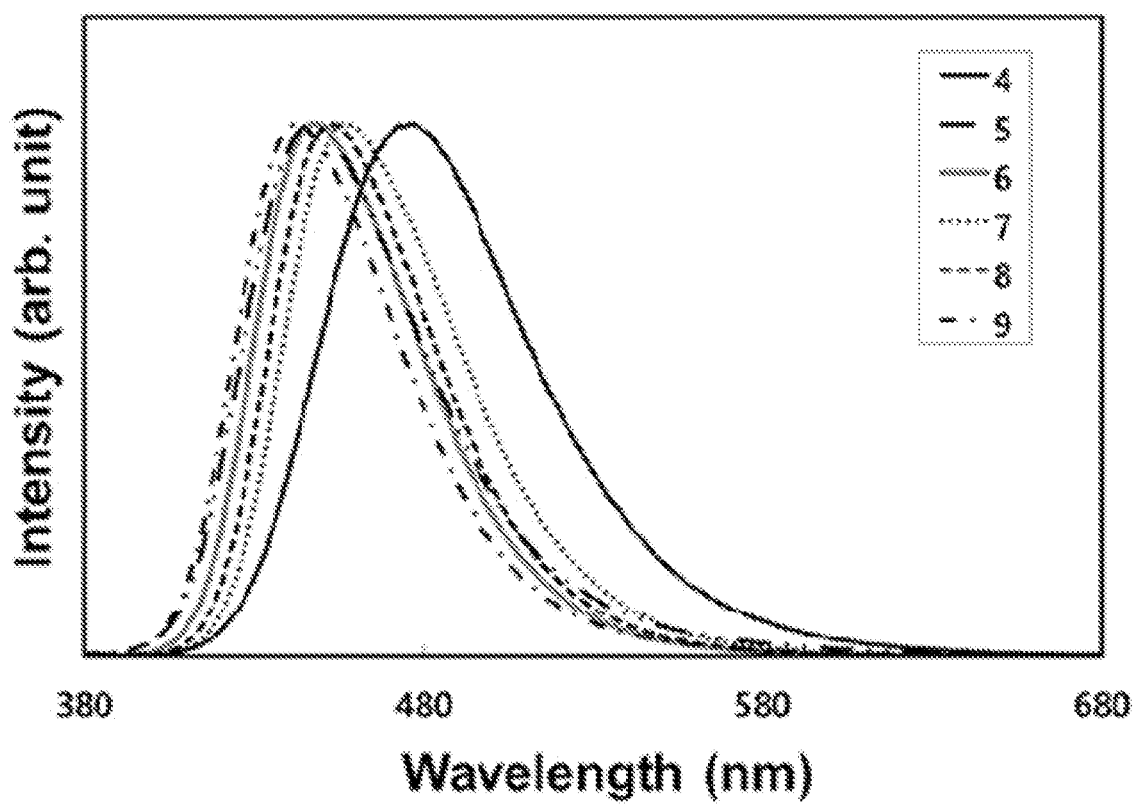
FIG. 2 shows emission spectra measured for first to sixth organic light emitting devices.
Figure 3:
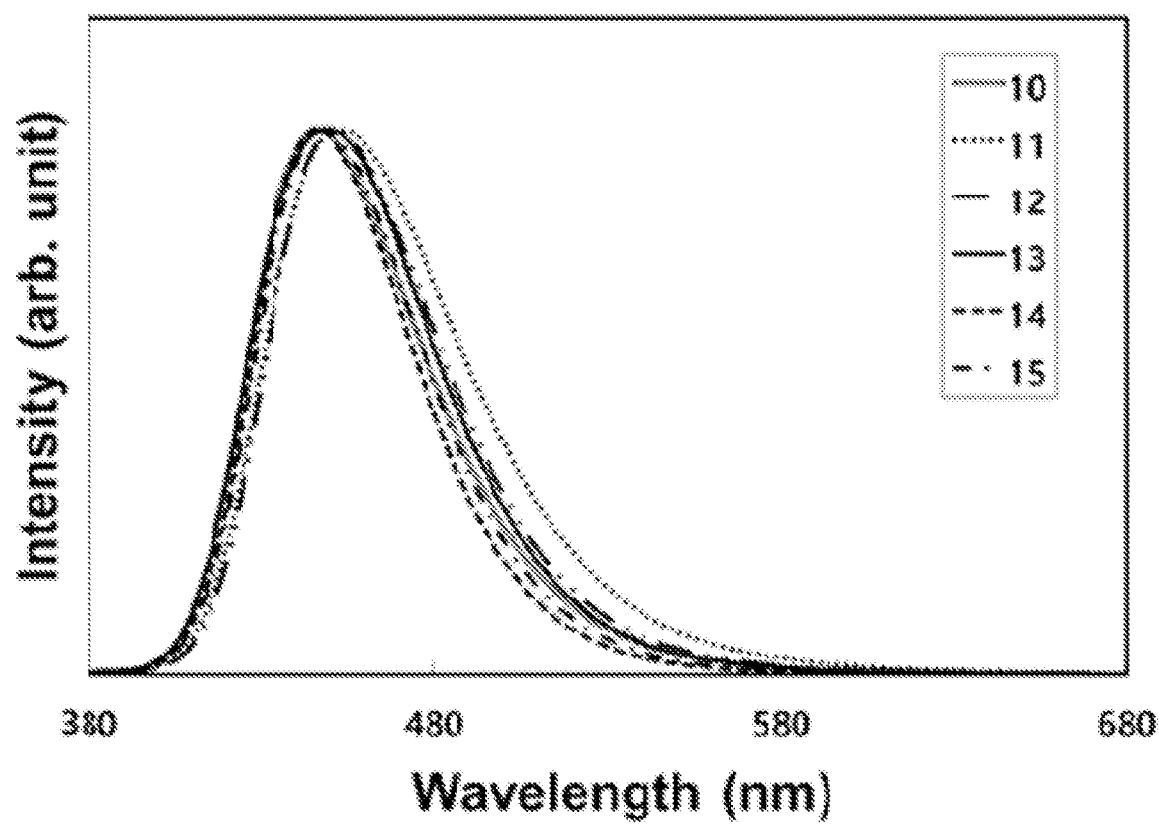
FIG. 3 shows emission spectra measured for seventh to twelfth organic light emitting devices.

FIG. 2 shows emission spectra measured for first to sixth organic light emitting devices, and FIG. 3 shows emission spectra measured for seventh to twelfth organic light emitting devices.

Referring to FIG. 2, it may be confirmed that all of the first to sixth organic light emitting devices emit blue light with a very narrow full width at half maximum (FWHM). Specifically, the first organic light emitting device 4 emits blue light having a peak wavelength of 476 nm and an FWHM of 71 nm. The second organic light emitting device 5 emits blue light having a peak wavelength of 447 nm and a FWHM of 60 nm. The third organic light emitting device 6 emits blue light having a peak wavelength of 449 nm and an FWHM of 56 nm. The fourth organic light emitting device 7 emits blue light having a peak wavelength of 456 nm and a FWHM of 60 nm. The fifth organic light emitting device 8 emits blue light having a peak wavelength of 454 nm and a FWHM of 56 nm. The sixth organic light emitting device 9 emits blue light having a peak wavelength of 443 nm and a FWHM of 55 nm.

Referring to FIG. 3, it may be confirmed that all of the seventh to twelfth organic light emitting devices emit blue light with a very narrow full width at half maximum (FWHM). Specifically, the seventh organic light emitting device 10 emits blue light having a peak wavelength of 448 nm and an FWHM of 58 nm. The eighth organic light emitting device 11 emits blue light having a peak wavelength of 450 nm and a FWHM of 66 nm. The ninth organic light emitting device 12 emits blue light having a peak wavelength of 449 nm and an FWHM of 59 nm. The tenth organic light emitting device 13 emits blue light having a peak wavelength of 450 nm and a FWHM of 62 nm. The eleventh organic light emitting device 14 emits blue light having a peak wavelength of 448 nm and a FWHM of 54 nm. The twelfth organic light emitting device 15 emits blue light having a peak wavelength of 449 nm and a FWHM of 56 nm.

While the foregoing disclosure has been described with reference to preferred present examples of the present disclosure, those skilled in the art will appreciate that various modifications may be made to the present disclosure without departing from the spirit and scope of the present disclosure set forth in the following claims. That is, changes may be made without departing from the spirit and scope of the invention.

What is claimed is:

1. A delayed fluorescence material having a molecular structure, wherein the molecular structure includes an electron donor unit and an electron acceptor unit coupled to the electron donor unit, wherein the electron acceptor unit includes an indolocarbazole group having at least one acceptor functional-group bound to the indolocarbazole group, wherein the molecular structure has one of following structures 1-3 and 1-6:

[Structural formula 1-3]

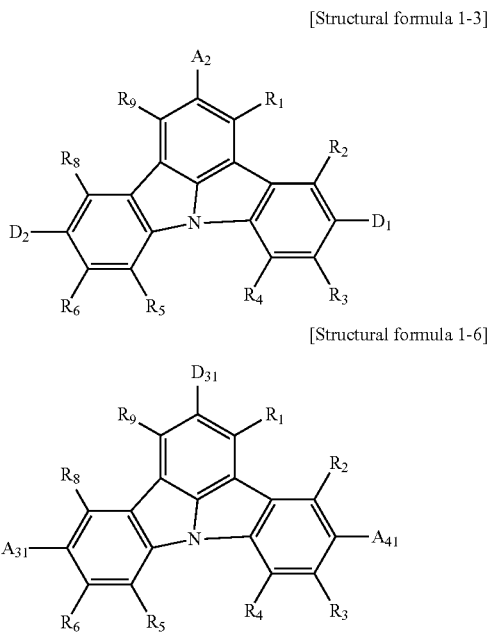

[Structural formula 1-6]

[Structural formula 3-1]
[Structural formula 3-2]

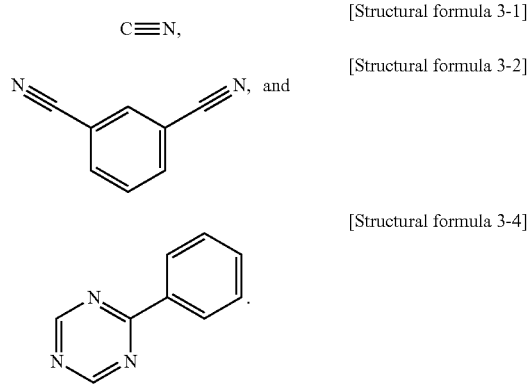

[Structural formula 3-4]

2. The delayed fluorescence material of claim 1, wherein each of $D_1$, $D_2$ and $D_{31}$ individually includes a functional-group compound derived from one selected from a group consisting of compounds having following structural formulas 2-1 to 2-52 respectively:

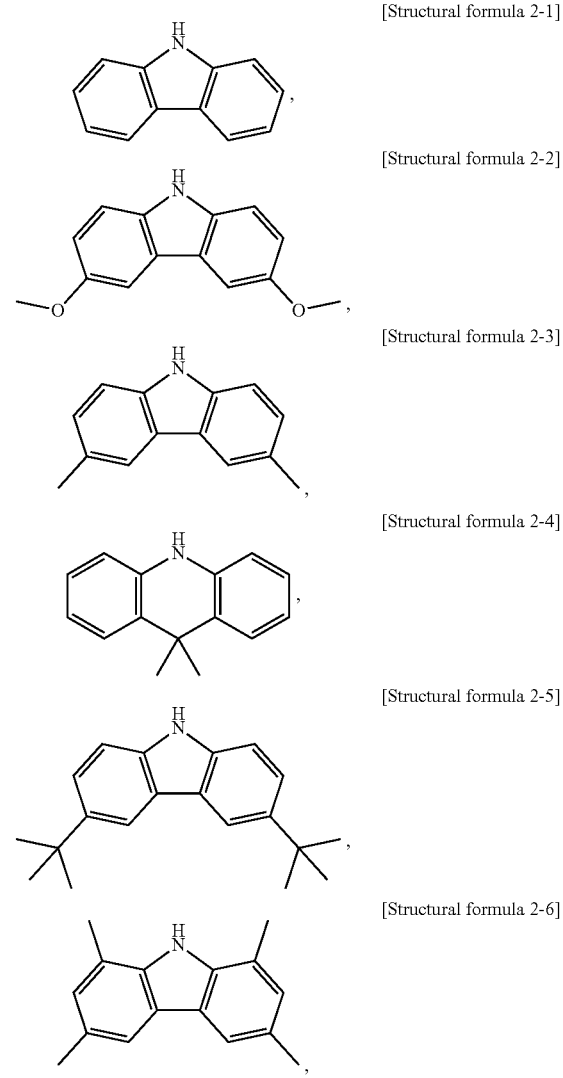

where each of $D_1$, $D_2$, and $D_{31}$ individually represents the electron donor unit, wherein each of $A_2$, $A_{31}$ and $A_{41}$ individually represents the acceptor functional-group, and wherein each of $R_1$ to $R_9$ individually represents one selected from a group consisting of hydrogen, deuterium, an alkyl group having 1 to 60 carbon atoms, an alkylthio group having 1 to 10 carbon atoms, an alkyl-substituted amino group having 1 to 10 carbon atoms, an aralkyl group having 7 to 20 carbon atoms, a diarylamino group having 12 to 24 carbon atoms, an alkoxycarbonyl group having 2 to 10 carbon atoms, an alkylsulfonyl group having 1 to 10 carbon atoms, a haloalkyl group having 1 to 10 carbon atoms, an amino group, an alkylamide group having 2 to 10 carbon atoms, a trialkylsilyl group having 3 to 20 carbon atoms, a trialkylsilylalkyl group having 4 to 20 carbon atoms, an alkenyl group having 2 to 60 carbon atoms, a trialkylsilylalkenyl group having 5 to 20 carbon atoms, an alkynyl group having 2 to 60 carbon atoms, a trialkylsilylalkynyl group having 5 to 20 carbon atoms, a cyano group, a nitro group, an aryl group having 6 to 60 carbon atoms, a heteroaryl group having 3 to 60 carbon atoms, an alkoxy group having 1 to 60 carbon atoms, an aryloxy group having 6 to 60 carbon atoms, an arylalkyl group having 7 to 60 carbon atoms, a heteroarylalkyl group having 3 to 60 carbon atoms, a cycloalkyl group having 3 to 60 carbon atoms, a heterocycloalkyl group having 1 to 60 carbon atoms, an alkylsilyl group having 3 to 60 carbon atoms, an arylsilyl group having 3 to 60 carbon atoms, a heteroarylsilyl group having 1 to 60 carbon atoms, and a substituted or unsubstituted aromatic 6-membered heterocycle having 3 to 30 carbon atoms, wherein at least two of $R_1$ to $R_9$ are the same or different, or adjacent two of $R_1$ to $R_9$ are coupled to form a ring, and wherein at least one of $A_2$, $A_{31}$ and $A_{41}$ individually includes a functional-group compound selected from a group consisting of compounds having following structural formulas 3-1, 3-2 and 3-4 respectively:

-continued
[Structural formula 2-7]
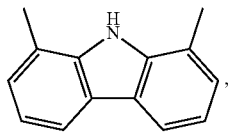
[Structural formula 2-8]
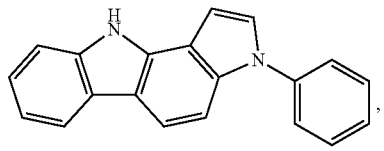
[Structural formula 2-9]
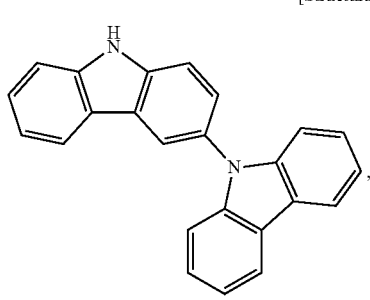
[Structural formula 2-10]
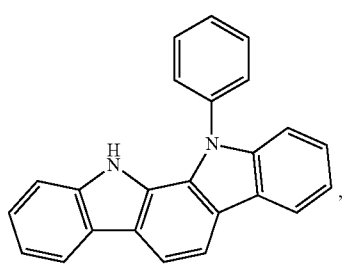
[Structural formula 2-11]
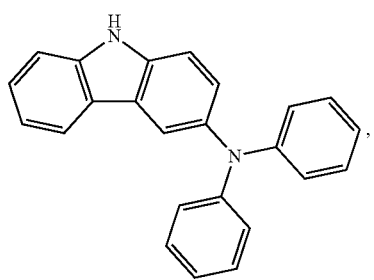
[Structural formula 2-12]
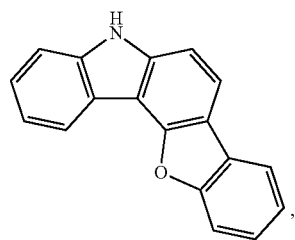
-continued
[Structural formula 2-13]
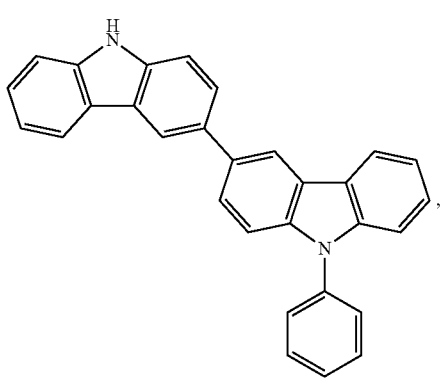
[Structural formula 2-14]
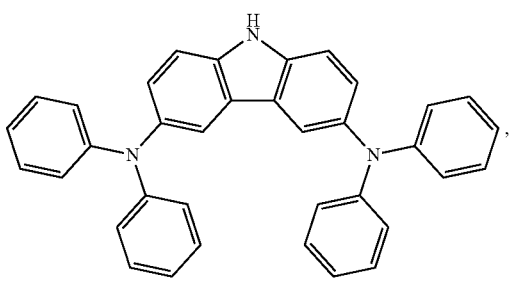
[Structural formula 2-15]
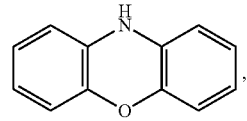
[Structural formula 2-16]
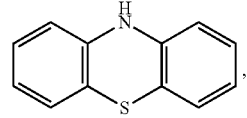
[Structural formula 2-17]
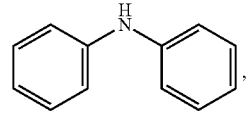
[Structural formula 2-18]
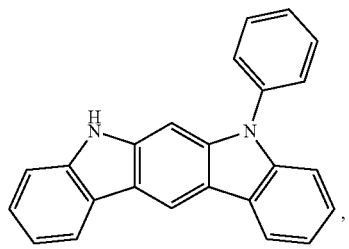
[Structural formula 2-19]
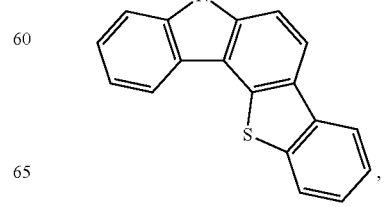

[Structural formula 2-20]
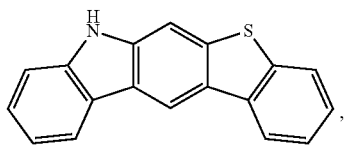
[Structural formula 2-21]
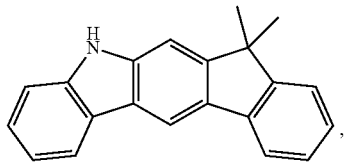
[Structural formula 2-22]
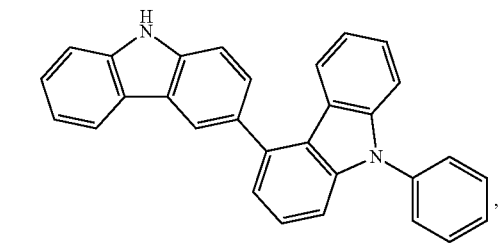
[Structural formula 2-23]
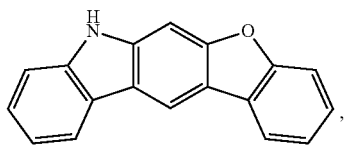
[Structural formula 2-24]
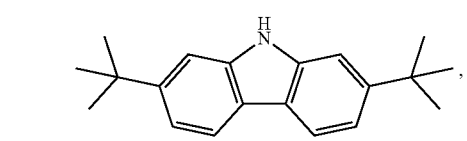
[Structural formula 2-25]
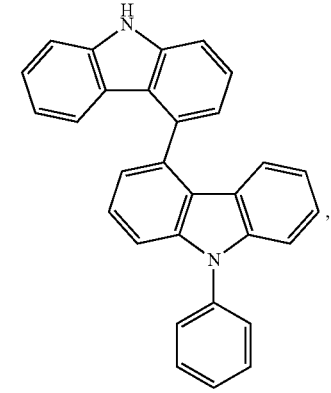
[Structural formula 2-26]
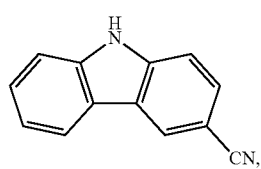
[Structural formula 2-27]
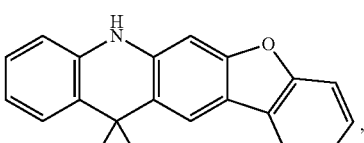
[Structural formula 2-28]
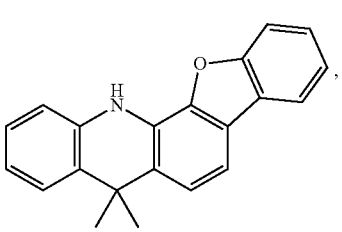
[Structural formula 2-29]
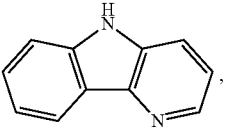
[Structural formula 2-30]
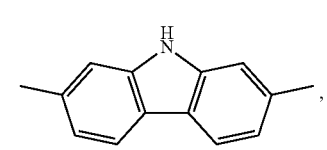
[Structural formula 2-31]
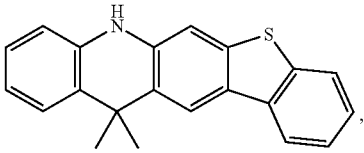
[Structural formula 2-32]
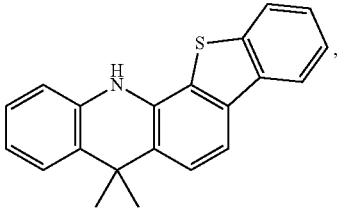
[Structural formula 2-33]
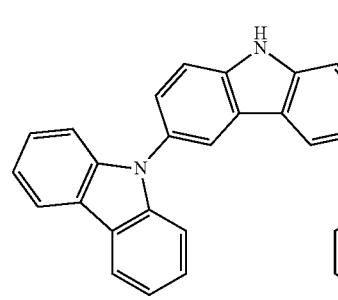
[Structural formula 2-34]
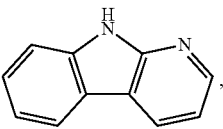

[Structural formula 2-35]
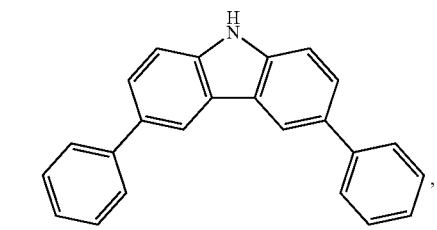
[Structural formula 2-36]
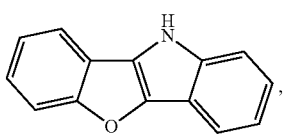
[Structural formula 2-37]
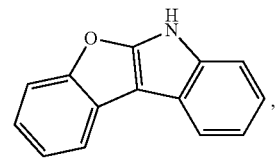
[Structural formula 2-38]
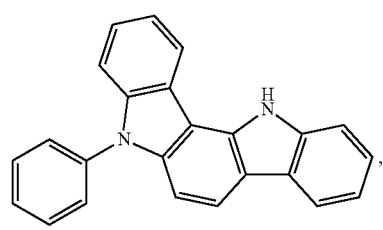
[Structural formula 2-39]
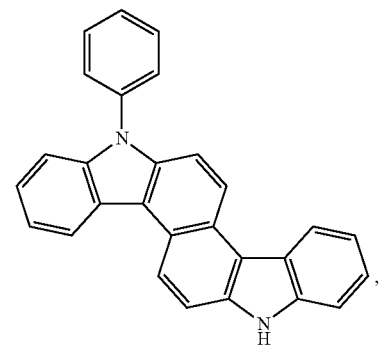
[Structural formula 2-40]
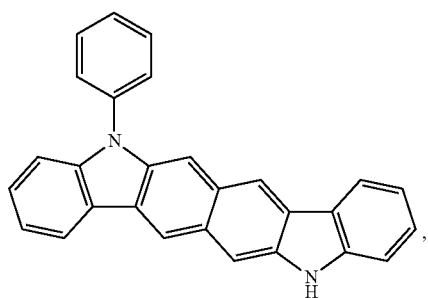
[Structural formula 2-41]
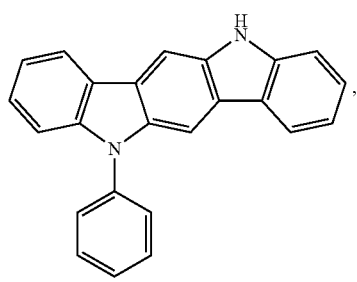
[Structural formula 2-42]
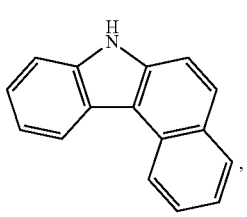
[Structural formula 2-43]
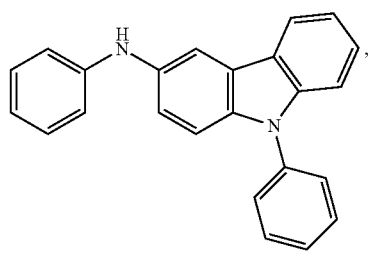
[Structural formula 2-44]
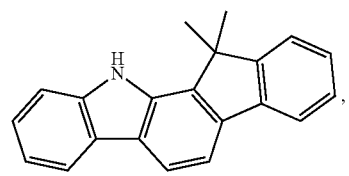
[Structural formula 2-45]
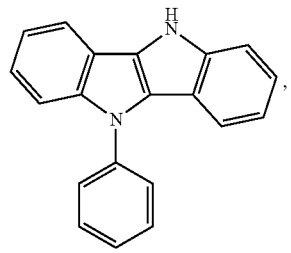
[Structural formula 2-46]
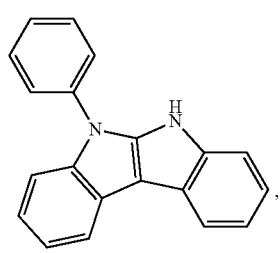

[Structural formula 2-47]
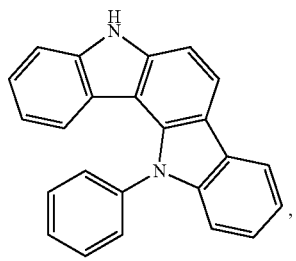
[Structural formula 2-48]
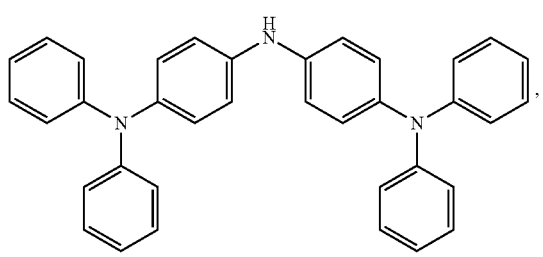
[Structural formula 2-49]
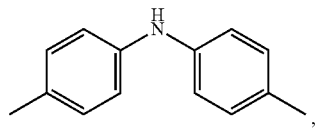
[Structural formula 2-50]
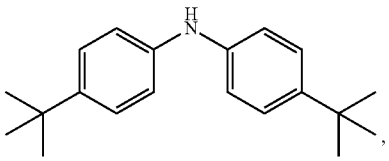
[Structural formula 2-51]
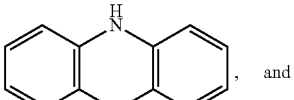
, and
[Structural formula 2-52]
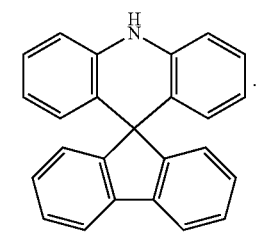
.
3. The delayed fluorescence material of claim 1, wherein the molecular structure has one of following structural formulas:
[Structural formula 4]
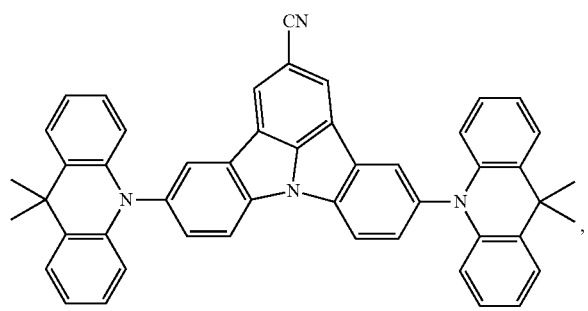
,
[Structural formula 5]
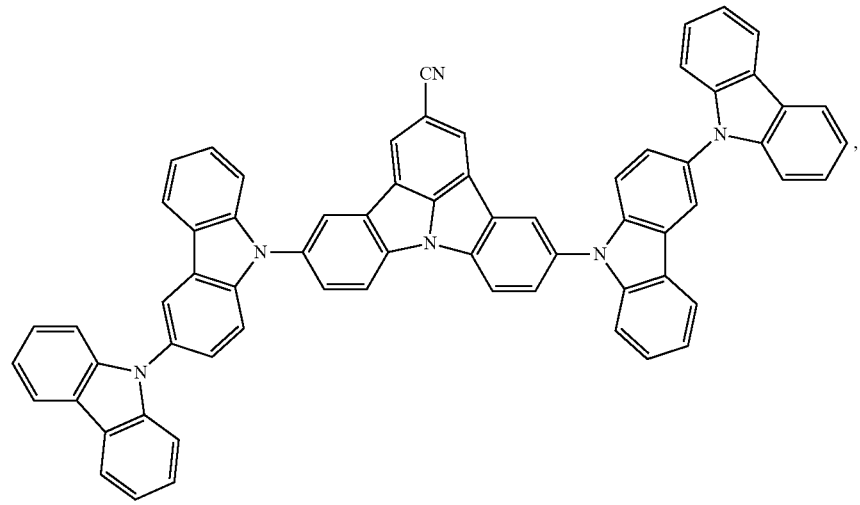
, -continued
[Structural formula 6]
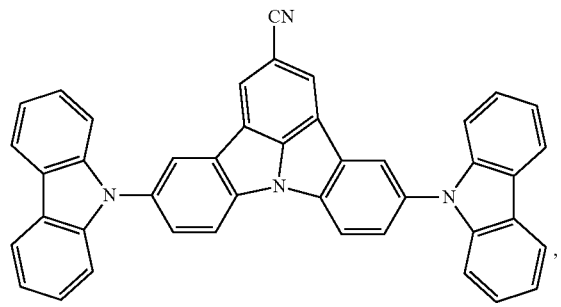
[Structural formula 7]
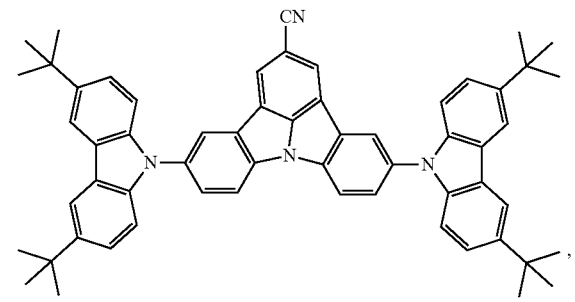
[Structural formula 8]
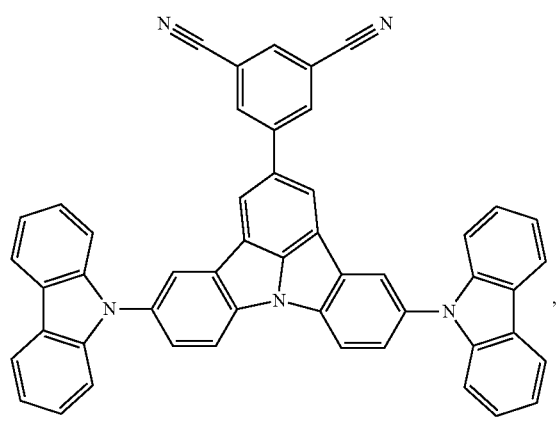
[Structural formula 10]
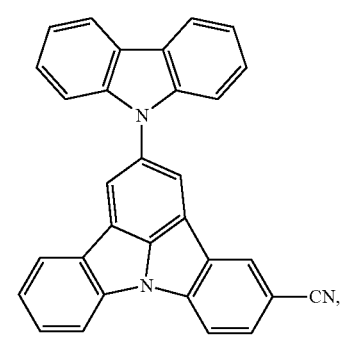
[Structural formula 12]
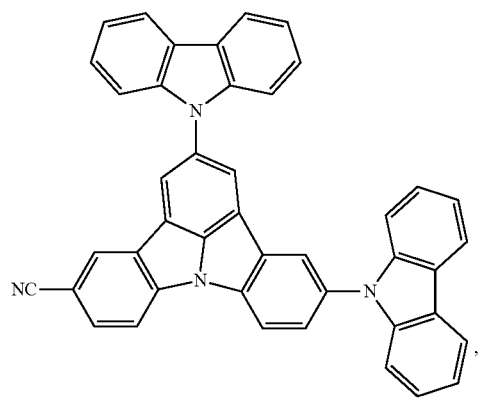
[Structural formula 14]
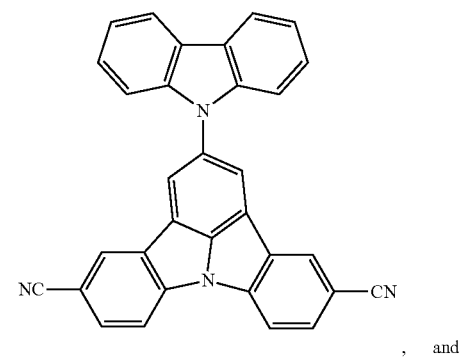
, and
[Structural formula 15]
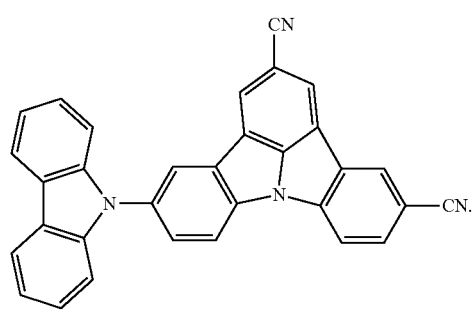

4. An organic light-emitting device including a light emission layer, wherein the layer contains the delayed fluorescence material of claim 1.

5. An organic light-emitting device including a light emission layer, wherein the layer contains the delayed fluorescence material of claim 2.

6. An organic light-emitting device including a light emission layer, wherein the layer contains the delayed fluorescence material of claim 3.

7. A delayed fluorescence material having a molecular structure of one of following structural formulas 1-1 to 1-6:

[Structural formula 1-1]

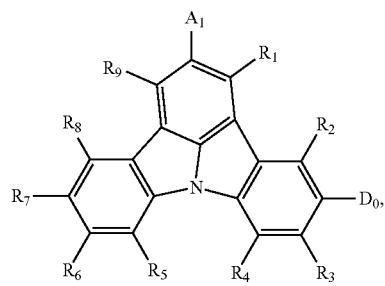

[Structural formula 1-2]

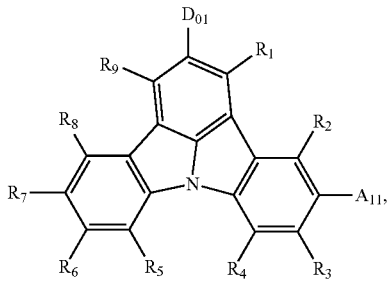

[Structural formula 1-3]

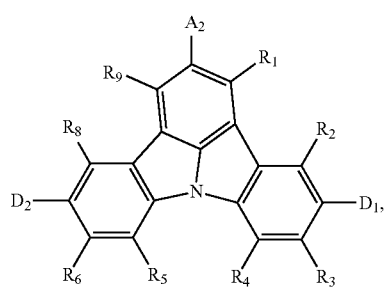

[Structural formula 1-4]

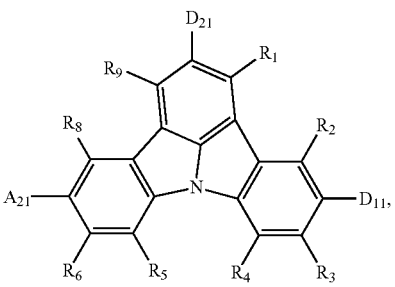

[Structural formula 1-5]

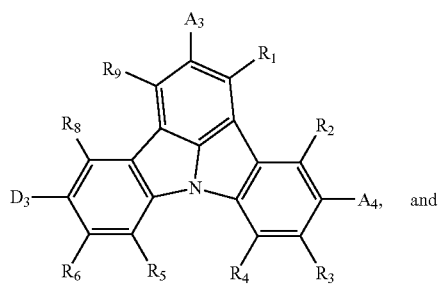

and

[Structural formula 1-6]

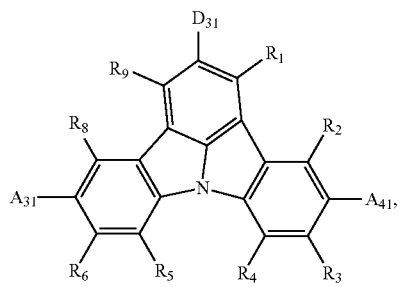

wherein each of $D_0$, $D_{01}$, $D_1$, $D_2$, $D_{11}$, $D_{21}$, $D_3$ and $D_{31}$ individually represents an electron donor unit that includes a functional-group compound derived from one selected from a group consisting of compounds having following structural formulas 2-2 to 2-52 respectively:

[Structural formula 2-2]

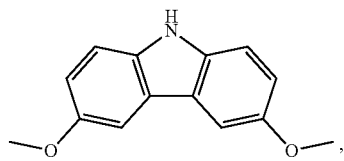

[Structural formula 2-3]

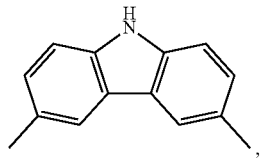

[Structural formula 2-4]

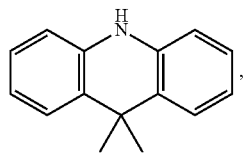

[Structural formula 2-5]

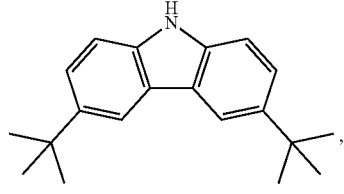

-continued
[Structural formula 2-6]
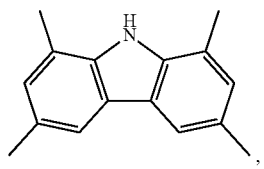
[Structural formula 2-7]
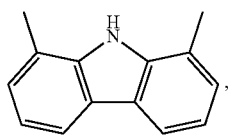
[Structural formula 2-8]
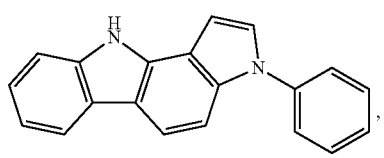
[Structural formula 2-9]
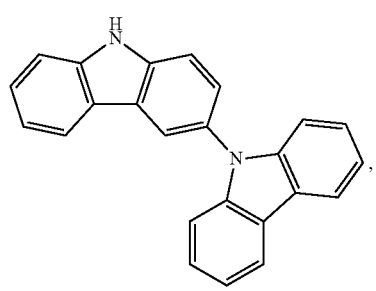
[Structural formula 2-10]
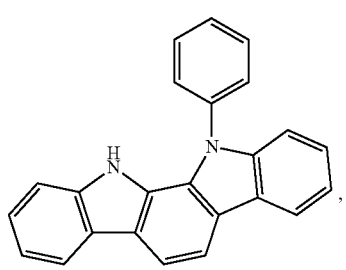
[Structural formula 2-11]
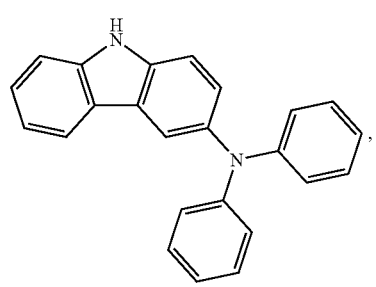
-continued
[Structural formula 2-12]
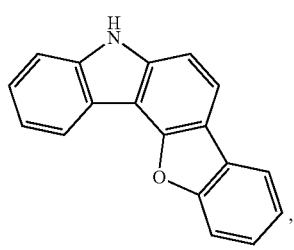
[Structural formula 2-13]
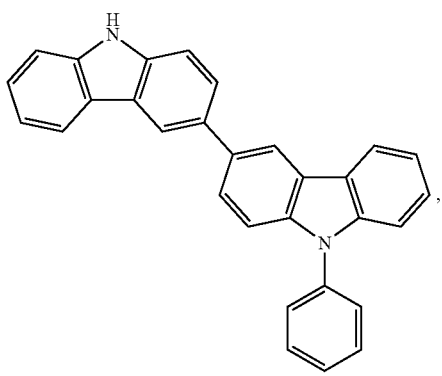
[Structural formula 2-14]
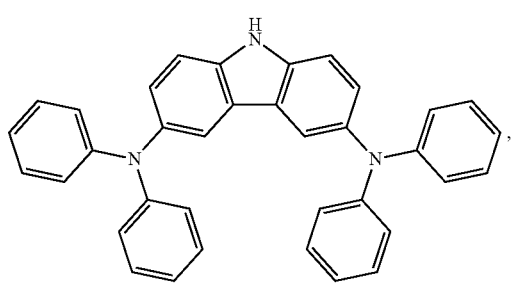
[Structural formula 2-15]
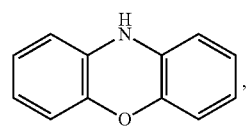
[Structural formula 2-16]
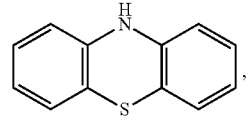
[Structural formula 2-17]
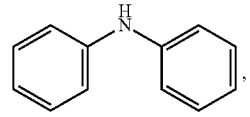
[Structural formula 2-18]
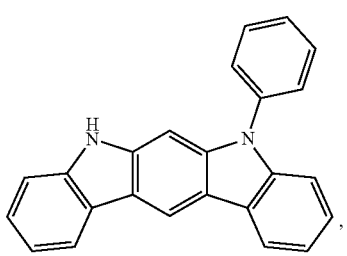

[Structural formula 2-19]
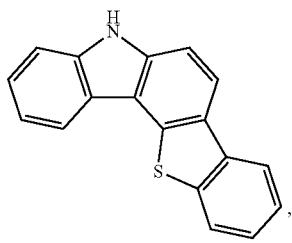
[Structural formula 2-20]
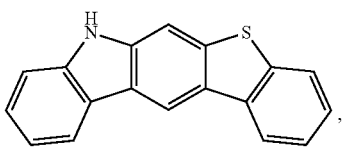
[Structural formula 2-21]
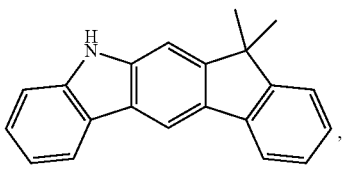
[Structural formula 2-22]
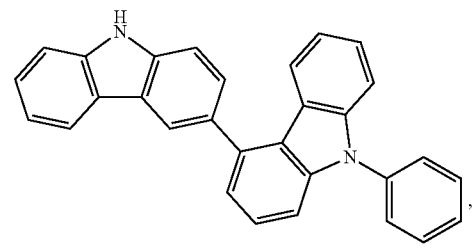
[Structural formula 2-23]
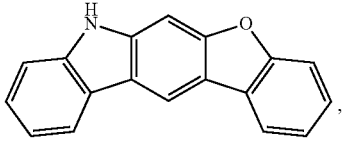
[Structural formula 2-24]
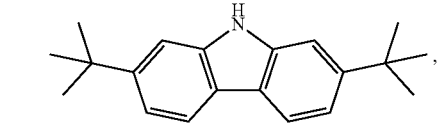
[Structural formula 2-25]
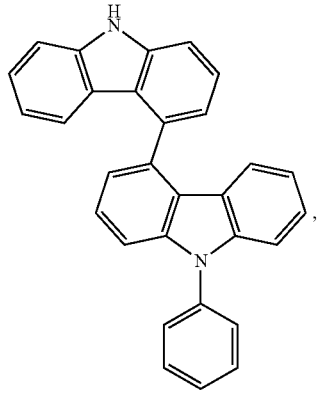
[Structural formula 2-26]
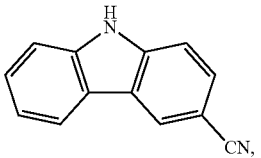
[Structural formula 2-27]
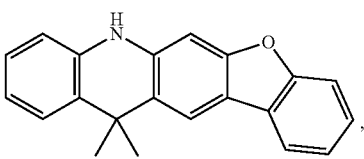
[Structural formula 2-28]
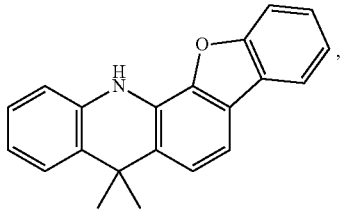
[Structural formula 2-29]
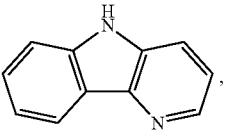
[Structural formula 2-30]
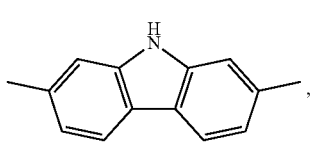
[Structural formula 2-31]
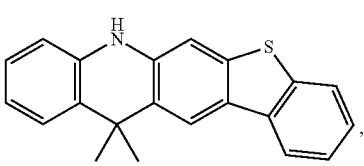
[Structural formula 2-32]
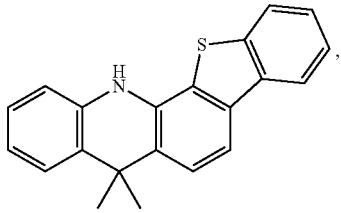
[Structural formula 2-33]
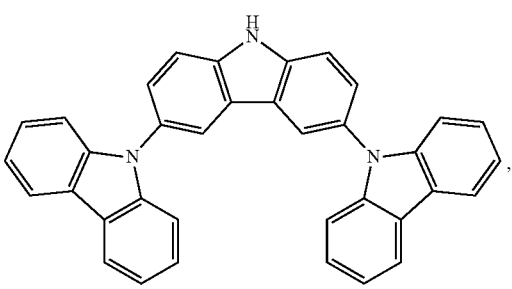

[Structural formula 2-34]
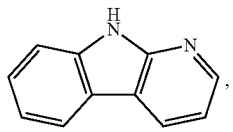
[Structural formula 2-35]
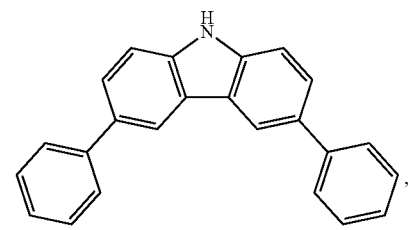
[Structural formula 2-36]
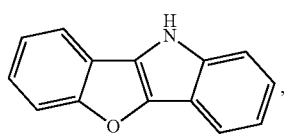
[Structural formula 2-37]
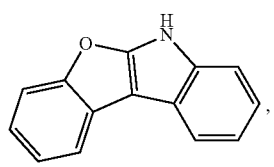
[Structural formula 2-38]
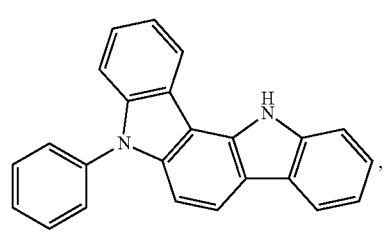
[Structural formula 2-39]
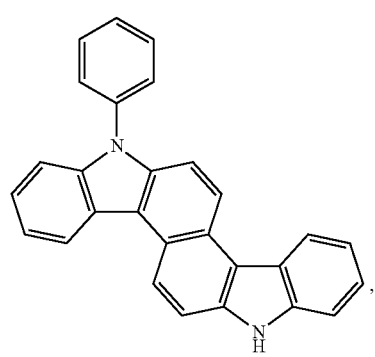
[Structural formula 2-40]
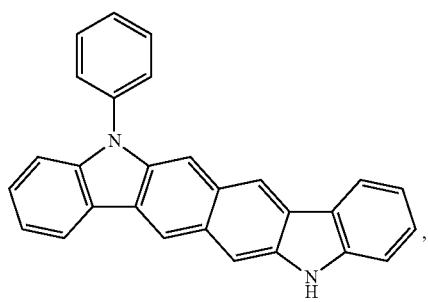
[Structural formula 2-41]
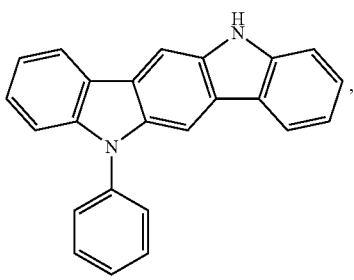
[Structural formula 2-42]
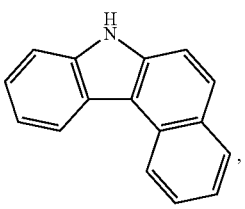
[Structural formula 2-43]
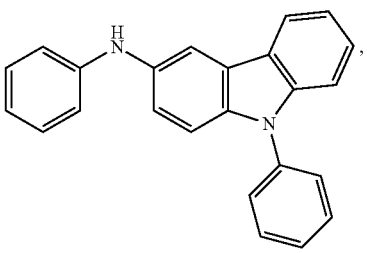
[Structural formula 2-44]
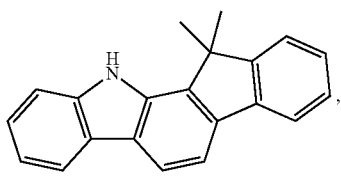
[Structural formula 2-45]
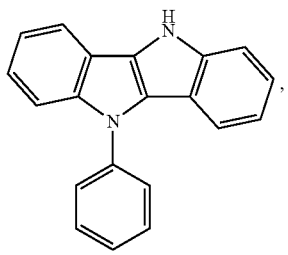
[Structural formula 2-46]
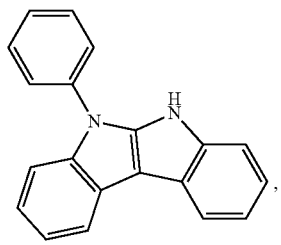

[Structural formula 2-47]

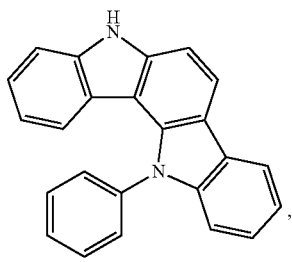

[Structural formula 2-48]

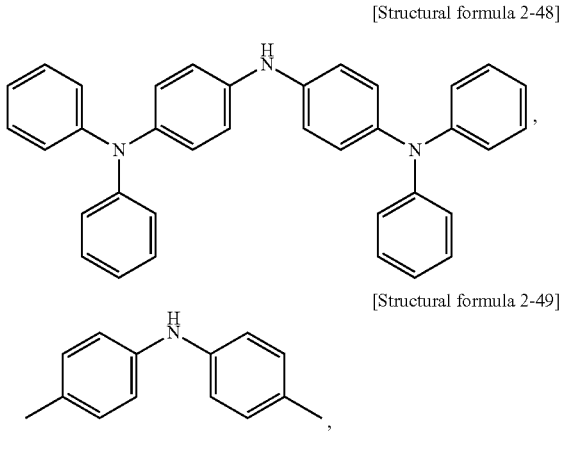

[Structural formula 2-49]

[Structural formula 2-50]

[Structural formula 2-51]

[Structural formula 2-52]

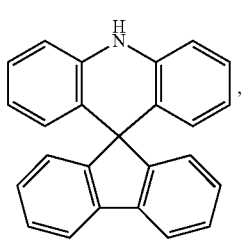

wherein each of $A_1$, $A_{11}$, $A_2$, $A_{21}$, $A_3$, $A_4$, $A_{31}$ and $A_{41}$ individually represents an acceptor functional-group that includes a functional-group compound selected from a group consisting of compounds having following structural formulas 3-1, 3-2 and 3-4 respectively:

[Structural formula 3-1]

[Structural formula 3-2]

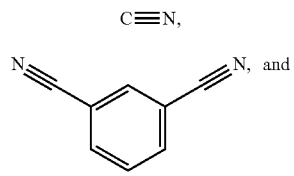

[Structural formula 3-4]

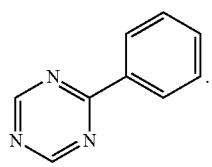

wherein each of $R_1$ to $R_9$ individually represents one selected from a group consisting of hydrogen, deuterium, an alkyl group having 1 to 60 carbon atoms, an alkylthio group having 1 to 10 carbon atoms, an alkyl-substituted amino group having 1 to 10 carbon atoms, an aralkyl group having 7 to 20 carbon atoms, a diarylamino group having 12 to 24 carbon atoms, an alkoxycarbonyl group having 2 to 10 carbon atoms, an alkylsulfonyl group having 1 to 10 carbon atoms, a haloalkyl group having 1 to 10 carbon atoms, an amino group, an alkylamide group having 2 to 10 carbon atoms, a trialkylsilyl group having 3 to 20 carbon atoms, a trialkylsilylalkyl group having 4 to 20 carbon atoms, an alkenyl group having 2 to 60 carbon atoms, a trialkylsilylalkenyl group having 5 to 20 carbon atoms, an alkynyl group having 2 to 60 carbon atoms, a trialkylsilylalkynyl group having 5 to 20 carbon atoms, a cyano group, a nitro group, an aryl group having 6 to 60 carbon atoms, a heteroaryl group having 3 to 60 carbon atoms, an alkoxy group having 1 to 60 carbon atoms, an aryloxy group having 6 to 60 carbon atoms, an arylalkyl group having 7 to 60 carbon atoms, a heteroarylalkyl group having 3 to 60 carbon atoms, a cycloalkyl group having 3 to 60 carbon atoms, a heterocycloalkyl group having 1 to 60 carbon atoms, an alkylsilyl group having 3 to 60 carbon atoms, an arylsilyl group having 3 to 60 carbon atoms, a heteroarylsilyl group having 1 to 60 carbon atoms, and a substituted or unsubstituted aromatic 6-membered heterocycle having 3 to 30 carbon atoms, wherein at least two of $R_1$ to $R_9$ are the same or different, or adjacent two of $R_1$ to $R_9$ are coupled to form a ring.

8. An organic light-emitting device including a light emission layer, wherein the layer contains the delayed fluorescence material of claim 7.

9. A delayed fluorescence material having a molecular structure, wherein the molecular structure includes an electron donor unit and an electron acceptor unit coupled to the electron donor unit, wherein the electron acceptor unit includes an indolocarbazole group having at least one acceptor functional-group bound to the indolocarbazole group, wherein the molecular structure has one of following structures 1-5 and 1-6:

[Structural formula 1-5]

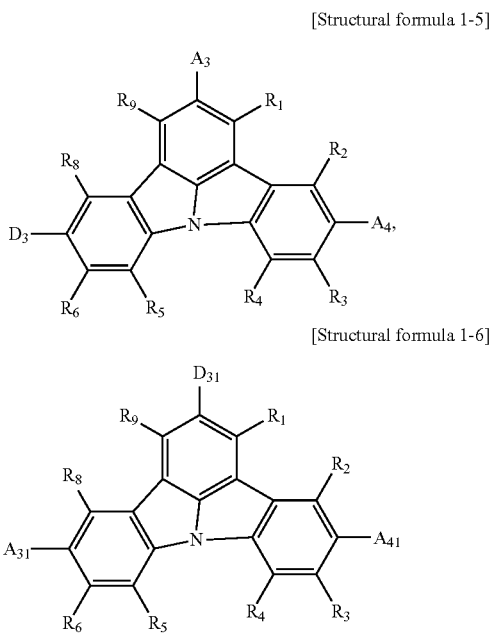

[Structural formula 1-6]

where each of $D_3$ and $D_{31}$ individually represents the electron donor unit, wherein each of $A_3$, $A_4$, $A_{31}$ and $A_{41}$ individually represents the acceptor functional-group, and wherein each of $R_1$ to $R_9$ individually represents one selected from a group consisting of hydrogen, deuterium, an alkyl group having 1 to 60 carbon atoms, an alkylthio group having 1 to 10 carbon atoms, an alkyl-substituted amino group having 1 to 10 carbon atoms, an aralkyl group having 7 to 20 carbon atoms, a diarylamino group having 12 to 24 carbon atoms, an alkoxycarbonyl group having 2 to 10 carbon atoms, an alkylsulfonyl group having 1 to 10 carbon atoms, a haloalkyl group having 1 to 10 carbon atoms, an amino group, an alkylamide group having 2 to 10 carbon atoms, a trialkylsilyl group having 3 to 20 carbon atoms, a trialkylsilylalkyl group having 4 to 20 carbon atoms, an alkenyl group having 2 to 60 carbon atoms, a trialkylsilylalkenyl group having 5 to 20 carbon atoms, an alkynyl group having 2 to 60 carbon atoms, a trialkylsilylalkynyl group having 5 to 20 carbon atoms, a cyano group, a nitro group, an aryl group having 6 to 60 carbon atoms, a heteroaryl group having 3 to 60 carbon atoms, an alkoxy group having 1 to 60 carbon atoms, an aryloxy group having 6 to 60 carbon atoms, an arylalkyl group having 7 to 60 carbon atoms, a heteroarylalkyl group having 3 to 60 carbon atoms, a cycloalkyl group having 3 to 60 carbon atoms, a heterocycloalkyl group having 1 to 60 carbon atoms, an alkylsilyl group having 3 to 60 carbon atoms, an arylsilyl group having 3 to 60 carbon atoms, a heteroarylsilyl group having 1 to 60 carbon atoms, and a substituted or unsubstituted aromatic 6-membered heterocycle having 3 to 30 carbon atoms, wherein at least two of $R_1$ to $R_9$ are the same or different, or adjacent two of $R_1$ to $R_9$ are coupled to form a ring.

10. An organic light-emitting device including a light emission layer, wherein the layer contains the delayed fluorescence material of claim 9.

\* \* \* \* \*